US011134906B2

(12) United States Patent
Park et al.

(10) Patent No.: US 11,134,906 B2
(45) Date of Patent: Oct. 5, 2021

(54) X-RAY DETECTOR, MOBILE DEVICE AND HOST DEVICE

(71) Applicant: SAMSUNG ELECTRONICS CO., LTD., Suwon-si (KR)

(72) Inventors: Jong Seo Park, Yongin-si (KR); Woong Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/838,524

(22) Filed: Apr. 2, 2020

(65) Prior Publication Data

US 2020/0229786 A1 Jul. 23, 2020

Related U.S. Application Data

(63) Continuation of application No. 16/451,897, filed on Jun. 25, 2019, now Pat. No. 10,646,193, which is a (Continued)

(30) Foreign Application Priority Data

Nov. 23, 2015 (KR) .................. 10-2015-0164292
Oct. 10, 2016 (KR) .................. 10-2016-0130569

(51) Int. Cl.
*A61B 6/00* (2006.01)
*H01L 27/146* (2006.01)
(Continued)

(52) U.S. Cl.
CPC .......... *A61B 6/4494* (2013.01); *A61B 6/4208* (2013.01); *A61B 6/465* (2013.01);
(Continued)

(58) Field of Classification Search
CPC .......... A61B 6/42; A61B 6/4208; A61B 6/44; A61B 6/4405; A61B 6/4494; A61B 6/46;
(Continued)

(56) References Cited

U.S. PATENT DOCUMENTS 10,433,809 B2 * 10/2019 Park .................. H04W 4/80
10,646,193 B2 * 5/2020 Park .................. A61B 6/56
(Continued)

FOREIGN PATENT DOCUMENTS

CN 103479371 A 1/2014
KR 10-1368751 3/2014
(Continued)

OTHER PUBLICATIONS

Korean Patent Office Action issued in Korean Patent Application No. 10-2018-0098867 dated May 20, 2019.
(Continued)

*Primary Examiner* — Anastasia Midkiff
(74) *Attorney, Agent, or Firm* — Staas & Halsey LLP

(57) ABSTRACT

A mobile device, a host device, and an X-ray detector are provided. The mobile device includes a first communicator configured to receive identification information of the X-ray detector from the X-ray detector, and a second communicator configured to send the received identification information of the X-ray detector to the host device.

6 Claims, 33 Drawing Sheets

Related U.S. Application Data continuation of application No. 15/359,800, filed on Nov. 23, 2016, now Pat. No. 10,433,809.

(51) Int. Cl.
| | |
|---|---|
| *H04B 1/3827* | (2015.01) |
| *H04W 84/14* | (2009.01) |
| *H04B 5/00* | (2006.01) |
| *H04W 4/80* | (2018.01) |
| *H04W 84/20* | (2009.01) |
| *H04B 5/02* | (2006.01) |

(52) U.S. Cl.
CPC .............. *A61B 6/548* (2013.01); *A61B 6/566* (2013.01); *H01L 27/14601* (2013.01); *H04B 1/3833* (2013.01); *H04B 5/0056* (2013.01); *H04B 5/0062* (2013.01); *H04W 84/14* (2013.01); *A61B 6/42* (2013.01); *A61B 6/46* (2013.01); *A61B 6/461* (2013.01); *A61B 6/467* (2013.01); *A61B 6/54* (2013.01); *A61B 6/545* (2013.01); *A61B 6/563* (2013.01); *A61B 2560/0271* (2013.01); *A61B 2560/0487* (2013.01); *A61B 2562/08* (2013.01); *H04B 1/3827* (2013.01); *H04B 5/0031* (2013.01); *H04B 5/02* (2013.01); *H04B 2001/3861* (2013.01); *H04W 4/80* (2018.02); *H04W 84/20* (2013.01)

(58) Field of Classification Search
CPC ......... A61B 6/461; A61B 6/465; A61B 6/467; A61B 6/5294; A61B 6/54; A61B 6/545; A61B 6/548; A61B 6/56; A61B 6/566; A61B 2560/00; A61B 2560/02; A61B 2560/0266; A61B 2560/0271; A61B 2560/0487; A61B 2562/08; G01N 2223/00; G01N 2223/30; G01N 2223/301; H01L 24/146; H01L 24/14601; H01L 27/146; H01L 27/14601; H04W 84/00; H04W 84/02; H04W 84/10; H04W 84/12; H04W 84/14; H04W 84/18; H04W 84/20; H04W 92/00; H04W 92/08; H04W 92/10; H04B 1/00; H04B 1/02; H04B 1/034; H04B 1/0343; H04B 1/0346; H04B 1/06; H04B 1/086; H04B 1/38; H04B 1/3827; H04B 1/3833; H04B 1/385; H04B 5/00; H04B 5/0025; H04B 5/0031; H04B 5/0056; H04B 5/0062; H04B 5/02; H04B 2001/3861
See application file for complete search history.

(56) References Cited

U.S. PATENT DOCUMENTS

| | | | |
|---|---|---|---|
| 2004/0086164 A1 | 5/2004 | Moriyama et al. |
| 2006/0094936 A1 | 5/2006 | Russ |
| 2010/0169423 A1 | 7/2010 | Eguchi |
| 2011/0116486 A1 | 5/2011 | Tachikawa |
| 2011/0274244 A1 | 11/2011 | Jabri et al. |
| 2011/0306882 A1 | 12/2011 | Hannon et al. |
| 2012/0177183 A1 | 7/2012 | Liu et al. |
| 2012/0201355 A1 | 8/2012 | Butzine et al. |
| 2013/0188629 A1 | 7/2013 | Lemaire et al. |
| 2013/0329860 A1 | 12/2013 | Nonaka |
| 2014/0177806 A1 | 6/2014 | Tachikawa et al. |
| 2014/0362975 A1 | 12/2014 | Garcia et al. |
| 2015/0324680 A1 | 11/2015 | Berger et al. |
| 2016/0106385 A1 | 4/2016 | Park et al. |

FOREIGN PATENT DOCUMENTS

| | | |
|---|---|---|
| KR | 10-2015-0015246 | 2/2015 |
| KR | 10-2015-0039507 | 4/2015 |
| KR | 10-2015-0053697 | 5/2015 |
| KR | 10-2016-0045558 | 4/2016 |
| KR | 10-2016-0045559 | 4/2016 |
| WO | WO 2012/100118 A1 | 7/2012 |

OTHER PUBLICATIONS

Article by RF Wireless World, pp. 1-4, 2012. http://www.rfwireless-world.com/Technology/Bluetooth-advantages-and-disadvantages.html (Year: 2012).
Notice of Allowance dated Apr. 9, 2019 in U.S. Appl. No. 15/359,800.
Final Office Action dated Jan. 18, 2019 in U.S. Appl. No. 15/359,800.
Non-final Office Action dated Jun. 1, 2018 in U.S. Appl. No. 15/359,800.
Communication dated Feb. 23, 2017 issued by the International Searching Authority in counterpart International Application No. PCT/KR2016/013530 (PCT/ISA/210).
Communication dated Nov. 2, 2018, issued by the Korean Intellectual Property Office in counterpart Korean Patent Application No. 10-2018-0098867.
Communication dated Oct. 5, 2018, issued by European Patent Office in counterpart European Application No. 16868865.3.
Communication dated Apr. 13, 2018, issued by the Korean Intellectual Property Office in counterpart Korean Patent Application No. 10-2016-0130569.
Communication dated May 23, 2018, issued by the Korean Intellectual Property Office in counterpart Korean Patent Application No. 10-2016-0130569.
Communication dated Nov. 9, 2017, issued by the Korean Intellectual Property Office in counterpart Korean Patent Application No. 10-2016-0130569.
Korean Office Action dated May 20, 2019 in corresponding Korean Patent Application No. 10-2018-0098867.
Korean Patent Office Action issued in Korean Patent Application No. 10-2019- 0101102 dated Sep. 19, 2019.
U.S. Office Action dated Aug. 27, 2019 in U.S. Appl. No. 16/451,897.
U.S. Notice of Allowance dated Jan. 2, 2020 in U.S. Appl. No. 16/451,897.
U.S. Corrected Notice of Allowance dated Feb. 25, 2020 in U.S. Appl. No. 16/451,897.
U.S. Appl. No. 16/451,897, filed Jun. 25, 2019, Jong Seo Park, et al., Samsung Electronics Co., Ltd.
U.S. Appl. No. 15/359,800 (now 10,433,809), filed Nov. 23, 2016, Jong Seo Park, et al., Samsung Electronics Co., Ltd.
Chinese Office Action dated Dec. 10, 2020, in corresponding Chinese Patent Application No. 201680067748.0.
Communication pursuant to Article 94(3) EPC dated Jan. 12, 2021, in corresponding European Patent Application No. 16 868 865.3.
Indian Office Action dated Mar. 19, 2021, in corresponding Indian Patent Application No. 201817016191.
Chinese Office Action dated Jul. 1, 2021, in corresponding Chinese Patent Application No. 201680067748.0.

\* cited by examiner

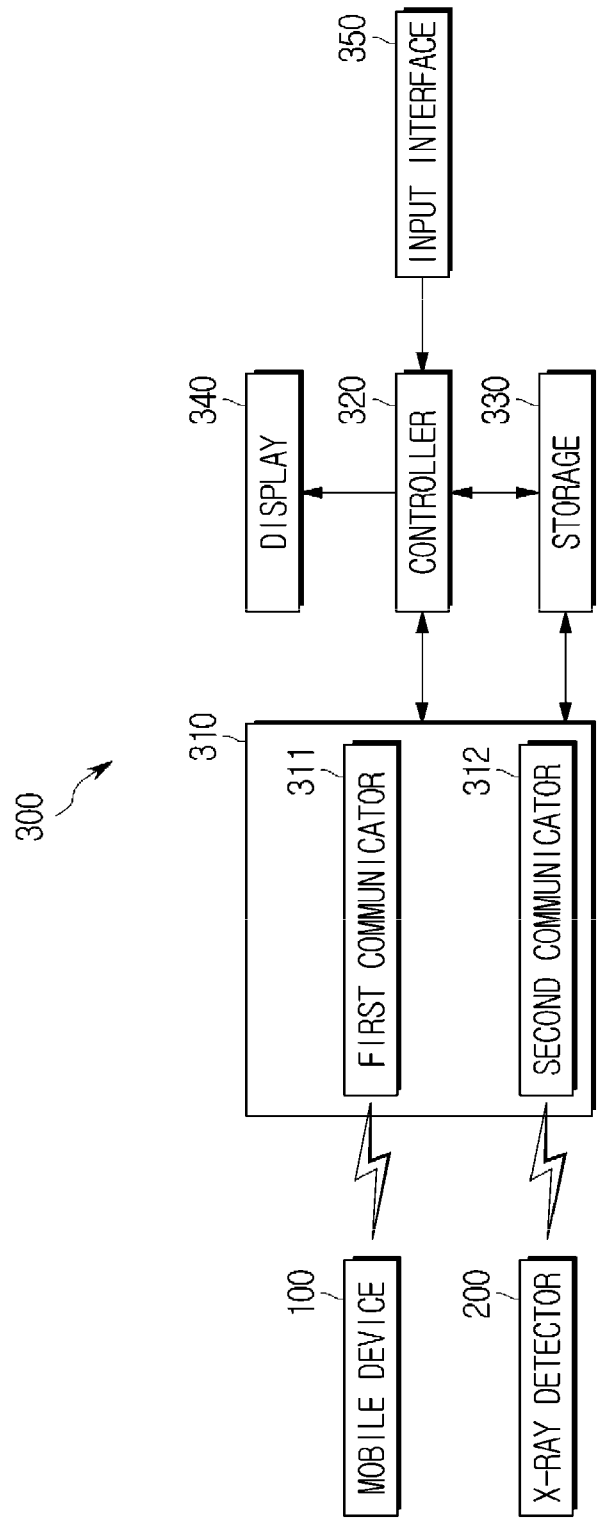

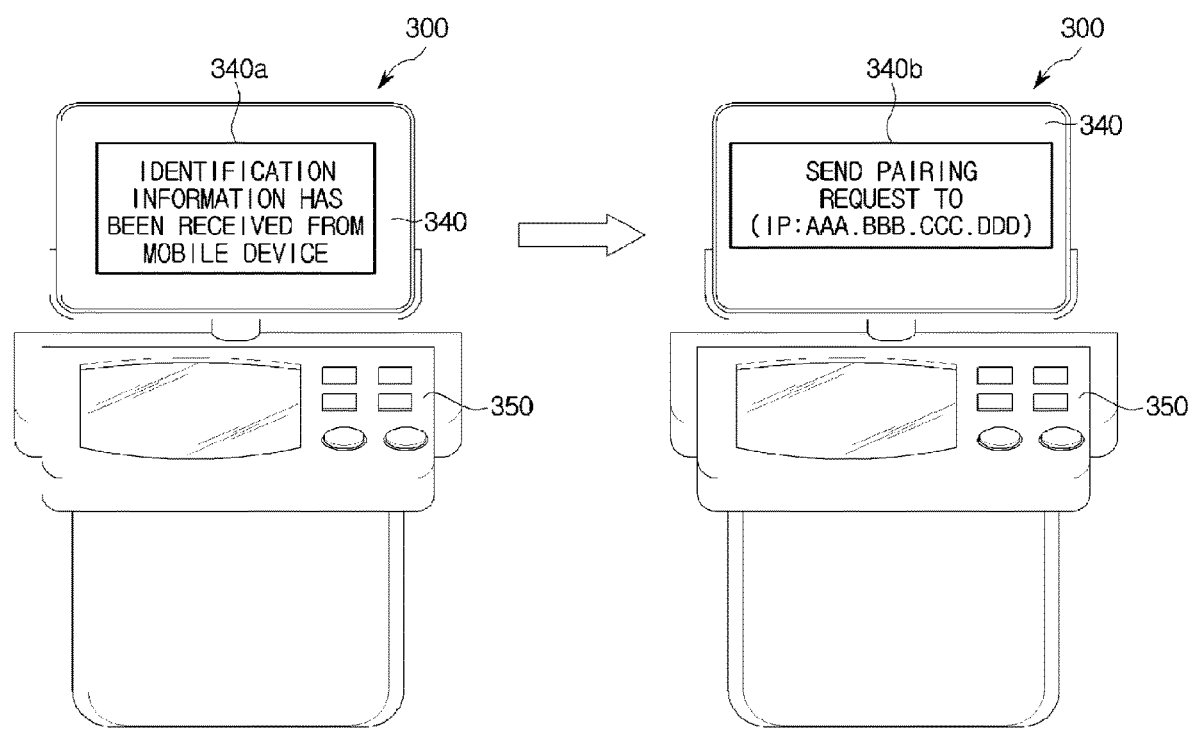

X-RAY DETECTOR, MOBILE DEVICE AND HOST DEVICE

CROSS-REFERENCE TO RELATED APPLICATION

This application is a continuation application of U.S. application Ser. No. 16/451,897 filed Jun. 25, 2019, which is a continuation application of U.S. application Ser. No. 15/359,800 filed Nov. 23, 2016, and claims the benefit of priority of the prior Korean Patent Application No. 10-2016-0130569, filed on Oct. 10, 2016, and Korean Patent Application No. 10-2015-0164292, filed on Nov. 23, 2015, the entire contents of which are incorporated herein by reference.

BACKGROUND

1. Field

Apparatuses and methods consistent with example embodiments relate to an X-ray detector paired with a host device, a mobile device used for pairing, a host device paired with an X-ray detector, an X-ray imaging apparatus including an X-ray detector, a host device, and a mobile device, and a method of pairing an X-ray detector with a host device.

2. Description of the Related Art

An X-ray detector is a device used to detect X-rays transmitted through an object and to image an internal structure of the object. When an X-ray detector detects X-rays and converts the detected X-rays into electric signals, a host device of an X-ray imaging apparatus processes the electric signals to generate an X-ray image indicating an anatomical structure of an object.

Recently, wireless X-ray detectors have been developed and used, and may be removable and thus used for various purposes.

To this end, wireless X-ray detectors perform a paring task for connecting an X-ray detector to be used with an X-ray imaging apparatus before X-ray imaging.

SUMMARY

Example embodiments may address at least the above problems and/or disadvantages and other disadvantages not described above. Also, the example embodiments are not required to overcome the disadvantages described above, and may not overcome any of the problems described above.

Example embodiments provide an X-ray detector, a mobile device, a host device, an X-ray imaging apparatus including an X-ray detector, a mobile device, and a host device, and an X-ray detector pairing method, in which an X-ray detector is simply and accurately paired with a host device through a mobile device, the mobile device is configured to simply and accurately pair the host device and the X-ray detector, and the host device is simply and accurately paired with the X-ray detector through the mobile device.

According to an aspect of an example embodiment, there is provided a mobile device including a first communicator configured to receive identification information of an X-ray detector from the X-ray detector, a second communicator, and a controller configured to control the second communicator to send the received identification information of the X-ray detector to a host device.

The first communicator may be further configured to receive detector information of the X-ray detector from the X-ray detector, the detector information having any one or any combination of a remaining battery capacity, a size, a resolution, a pixel size, calibration information, and a read-out rate of the X-ray detector.

The mobile device may further include a display configured to display either one or both of the detector information and a screen for receiving an approval of a pairing with the host device, and an input interface configured to receive an input of the approval of the pairing with the host device.

The first communicator may include any one or any combination of a Near Field Communication (NFC) module and a Radio Frequency Identification (RFID) reader, and is further configured to receive the identification information of the X-ray detector from the X-ray detector in response to the controller tagging the X-ray detector, the second communicator may include any one or any combination of a beacon and a Bluetooth Low Energy (BLE) module, and the controller may be further configured to control the second communicator to transmit a signal having the received identification information of the X-ray detector to the host device in response to the first communicator receiving the identification information of the X-ray detector.

The mobile device may further include a display configured to display a screen for receiving an approval of a pairing with the host device, before the sending of the received identification information of the X-ray detector to the host device or after the host device receives a pairing response from the X-ray detector.

According to an aspect of an example embodiment, there is provided a host device including a first communicator configured to receive identification information of an X-ray detector from a mobile device, a second communicator, and a controller configured to control the second communicator to send a pairing request having the received identification information to the X-ray detector.

The host device may further include a display configured to display a screen for receiving an approval of a pairing with the X-ray detector of which the identification information is received.

The host device may further include an input interface configured to receive an input of the approval of the pairing with the X-ray detector.

The controller may be further configured to control the second communicator to send a pairing approval request to the mobile device.

The second communicator may include any one or any combination of a Wi-Fi module and a Wi-Fi Direct module, and the controller may be further configured to control the second communicator to send the pairing request having the received identification information to the X-ray detector in response to the first communicator receiving the identification information of the X-ray detector.

The second communicator may be further configured to, in response to the host device being paired with the X-ray detector of which the identification information is received, receive X-ray data and detector information of the X-ray detector from the X-ray detector, the detector information having any one or any combination of a remaining battery capacity, a size, a resolution, a pixel size, a read-out rate, and calibration information of the X-ray detector.

The controller may be further configured to control the second communicator to release a pairing with the X-ray detector in response to the first communicator receiving identification information of a new X-ray detector.

According to an aspect of an example embodiment, there is provided an X-ray detector including a detector configured to detect an X-ray, and convert the detected X-ray into X-ray data, a first communicator configured to send identification information of the X-ray detector to a mobile device, a second communicator, and a controller configured to control the second communicator to pair a host device with the X-ray detector in response to the second communicator receiving a pairing request from the host device.

The first communicator may include any one or any combination of a Near Field Communication (NFC) tag and a Radio Frequency Identification (RFID) tag in which the identification information is recorded.

The second communicator may include any one or any combination of a Wi-Fi module and a Wi-Fi Direct module, and the controller may be further configured to control the second communicator to send a response to the host device to pair the X-ray detector and the host device in response to the second communicator receiving the pairing request from the host device.

BRIEF DESCRIPTION OF THE DRAWINGS

The above and/or other aspects of the disclosure will become apparent and more readily appreciated from the following description of example embodiments, taken in conjunction with the accompanying drawings of which:

FIG. 7A is a control block diagram of a workstation including different communication modules, according to an example embodiment.

FIGS. 9A and 9B are diagrams showing examples of a screen that may be displayed when a workstation receives identification information of an X-ray detector from a mobile device, according to an example embodiment;

DETAILED DESCRIPTION

Figure 1A:
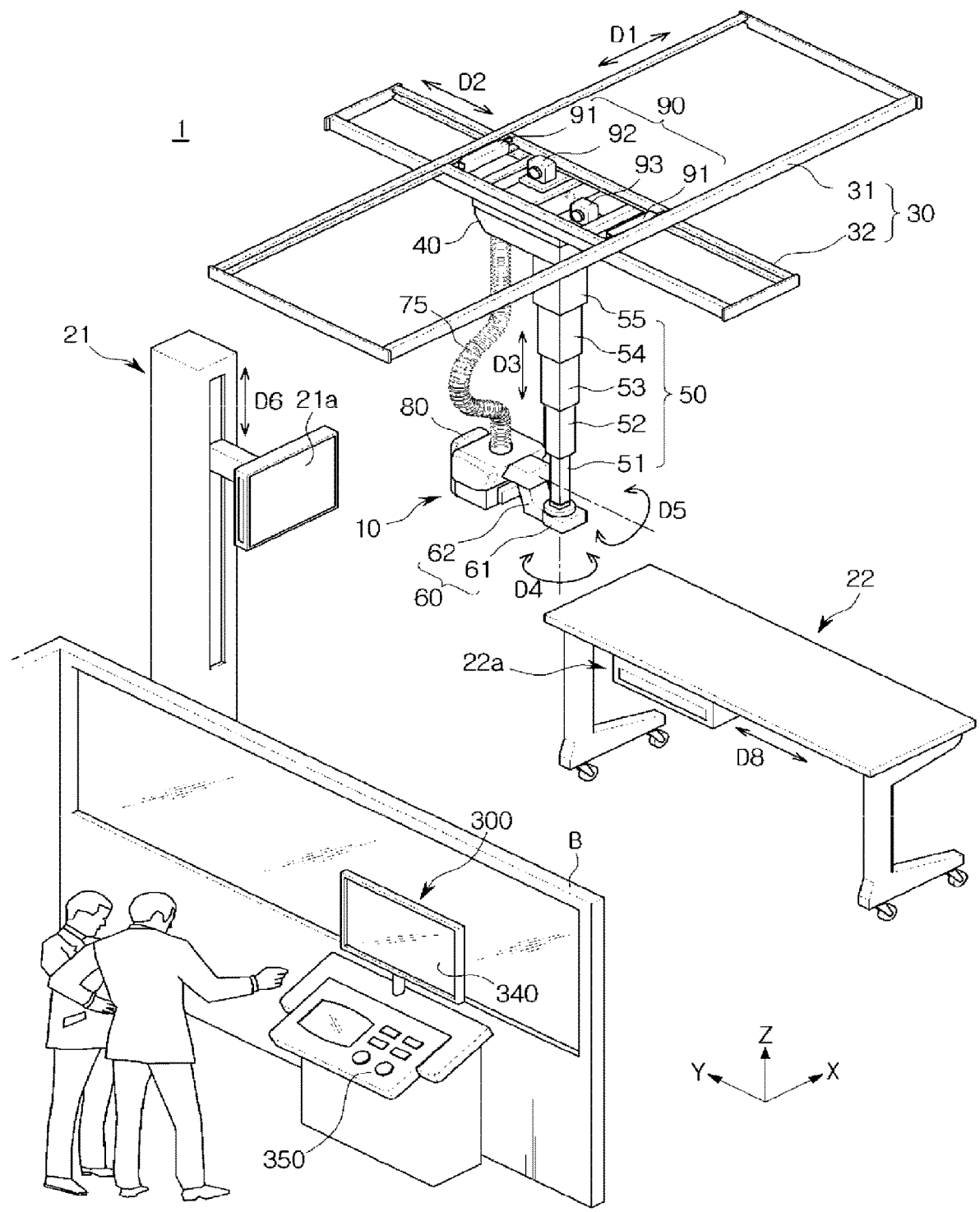
FIGS. 1A and 1B are diagrams showing an exterior appearance of an X-ray imaging apparatus according to an example embodiment.

Hereinafter, example embodiments of an X-ray detector, a mobile device, a workstation, an X-ray imaging apparatus, and a method of pairing an X-ray detector with a workstation will be described in detail with reference to the following drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions may not be described in detail because they would obscure the description with unnecessary detail.

It will be understood that the terms such as "unit," "-er (-or)," and "module" described in the specification refer to an element for performing at least one function or operation, and may be implemented in hardware, software, or the combination of hardware and software.

Figure 1B:
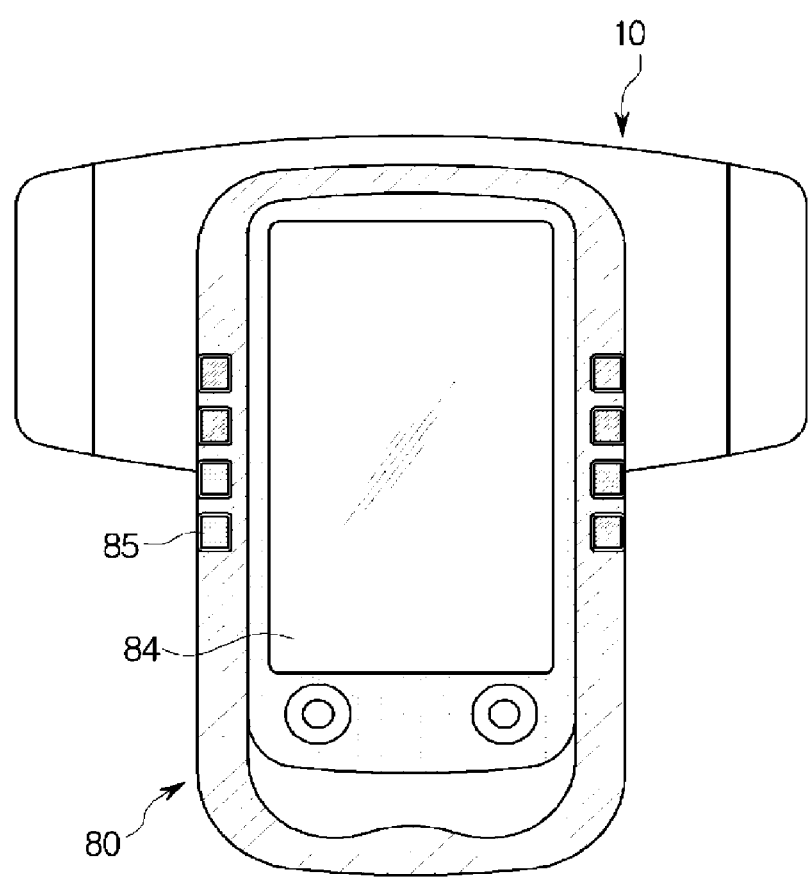

FIGS. 1A and 1B are diagrams showing an exterior appearance of an X-ray imaging apparatus according to an example embodiment.

The exterior appearance shown in FIG. 1A is an example of the X-ray imaging apparatus, which is a ceiling-type X-ray imaging apparatus with a tube head unit (THU) connected to a ceiling.

Referring to FIG. 1A, a guide rail 30 may be installed at a laboratory ceiling on which an X-ray imaging apparatus 1 is disposed, and a tube head unit (THU) 10 may be connected to a movable carriage 40 moving along the guide rail 30 and moved to a position corresponding to an object.

The guide rail 30 may include a first guide rail 31 and a second guide rail 32 that are installed to have a predetermined angle with respect to each other. As an example, the first guide rail 31 and the second guide rail 32 may be installed to be orthogonal to each other.

The first guide rail 31 may be installed at a laboratory ceiling, and the second guide rail 32 may be mounted on a lower side of the first guide rail 31 so that the second guide rail 32 may be slid. A roller movable along the first guide rail 31 may be installed at the first guide rail 31. The second guide rail 32 may be connected to the roller to move along the first guide rail 31.

A first direction D1 may be defined as a direction in which the first guide rail 31 extends, and a second direction D2 may be defined as a direction in which the second guide rail 32 extends. Accordingly, the first direction D1 and the second direction D2 may be orthogonal to each other and parallel with the laboratory ceiling.

The movable carriage 40 is disposed at a lower side of the second guide rail 32 so that the movable carriage 40 may move along the second guide rail 32. A roller provided to move along the second guide rail 32 may be installed at the movable carriage 40. Accordingly, the movable carriage 40 may move in the first direction D1 together with the second guide rail 32 and move in the second direction D2 along the second guide rail 32.

A post frame 50 is connected to the bottom of the movable carriage 40. The post frame 50 may include a plurality of posts 51, 52, 53, 54, and 55.

The plurality of posts 51, 52, 53, 54, and 55 are foldably connected to each other. The post frame 50 may be shortened in an upward direction of a laboratory or lengthened in a downward direction of the laboratory while being fixed to the movable carriage 40.

Because the THU 10 is coupled to the bottom of the post frame 50, a height of the THU 10 from the ground may be controlled by lengthening and shortening the post frame 50.

A third direction D3 may be defined as a direction in which the post frame 50 is lengthened or shortened. Accordingly, the third direction D3 may be orthogonal to the first direction D1 and the second direction D2.

The THU 10 is a device configured to emit an X-ray toward an object. The THU 10 may be an assembly including an X-ray tube that generates an X-ray and a collimator that adjusts an emission range of the generated X-ray and may be referred to as an X-ray source.

The THU 10 may be connected to the movable carriage 40 through a connection pipe 75. Various kinds of cables and electric wires that connect the THU 10 to other devices may built into the connection pipe 75, and also high voltage generated by a high-voltage generator may be supplied to the THU 10 through the connection pipe 75.

A rotatable joint 60 is disposed between the THU 10 and the post frame 50. The rotatable joint 60 combines the THU 10 with the post frame 50 and supports weight applied to the THU 10.

The rotatable joint 60 may include a first rotatable joint 61 connected to a lowest post 51 of the post frame 50 and a second rotatable joint 62 connected to the THU 10.

The first rotatable joint 61 is configured to rotate about a central axis of the post frame 50 that extends in a vertical direction of the laboratory. Accordingly, the first rotatable joint 61 may rotate on a plane perpendicular to the third direction D3. In this case, a rotational direction of the first rotatable joint 61 may be newly defined, and the newly-defined direction, which is a fourth direction D4, is a rotational direction of an axis parallel with the third direction D3.

The second rotatable joint 62 is configured to rotate on a plane perpendicular to the laboratory ceiling. Accordingly, the second rotatable joint 62 may rotate in a rotational direction of an axis parallel with the first direction D1 or the second direction D2. In this case, the rotational direction of the second rotatable joint 62 may be newly defined, and the newly-defined direction, which is a fifth direction D5, is a rotational direction of an axis extending in the first direction D1 or the second direction D2.

The THU 10 may be connected to the rotatable joint 60 to rotatably move in the fourth direction D4 and the fifth direction D5. A tilt angle of the THU 10 may be adjusted by rotating the second rotatable joint 62 in the fifth direction D5.

Also, the THU 10 may be connected to the post frame 50 by the rotatable joint 60 to linearly move in the first direction D1, the second direction D2, and the third direction D3.

A tube motor 90 may be provided to move the THU 10 in the first to fifth directions D1 to D5. The tube motor 90 may include an encoder that measures the number of rotations.

The tube motor 90 may include a plurality of motors 91, 92, and 93 corresponding to respective directions, each of which may be disposed at various positions in consideration of design convenience.

For example, the motor 91 that moves the second guide rail 32 in the first direction D1 may be disposed in the vicinity of the first guide rail 31, the motor 92 that moves the movable carriage 40 in the second direction D2 may be disposed in the vicinity of the second guide rail 32, and the motor 93 that increases or decreases the length of the post frame 50 in the third direction D3 may be disposed at the movable carriage 40.

Also, a motor that rotatably moves the THU 10 in the fourth direction D4 may be disposed in the vicinity of the first rotatable joint 61, a motor that rotatably moves the THU 10 in the fifth direction D5 may be disposed in the vicinity of the second rotatable joint 62.

Each of the motors may be connected to a power transfer unit to linearly or rotatably move the THU 10 in the first to fifth directions D1 to D5. The power transfer unit may be a belt and pulley system, a chain and sprocket system, a shaft, or the like that are generally used.

A control panel 80 that provides information to a user and receives a control command from the user as an input may be provided at one side of the THU 10. Here, the user is a person who takes an X-ray image of an object using the X-ray imaging apparatus 1, and may be medical staff including, but not limited to, a doctor, a radiologist, and a nurse. The user may include a person who can use the X-ray imaging apparatus 1.

An imaging table 22 and an imaging stand 21 that may be equipped with the X-ray detector 200 may be provided at a position adjacent to a movable range of the THU 10.

A detector mounting unit 22a is formed on the bottom of the imaging table 22 and is movable in a longitudinal direction (a direction D8) of the imaging table 22. The X-ray detector 200 is inserted into the detector mounting unit 22a. When an object is placed on the imaging table 22, the THU 10 and the detector mounting unit 22a may be moved to a position corresponding to a portion of the object to be imaged. Then, X-ray imaging may be performed.

Also, a detector mounting unit 21a may be formed on the imaging stand 21 to move in a longitudinal direction (a direction D6) of the imaging stand 21. The longitudinal direction of the imaging stand 21 is perpendicular to the longitudinal direction of the imaging table 22. The X-ray detector 200 is inserted into the detector mounting unit 21a. When an object is placed in front of the detector mounting unit 21a, the THU 10 and the detector mounting unit 21a may be moved to a position corresponding to a portion of the object to be imaged. Then, X-ray imaging may be performed.

The X-ray imaging apparatus 1 may include a motor for moving the detector mounting unit 22a of the imaging table 22 in the direction D8 and a motor for moving the detector mounting unit 21a of the imaging stand 21 in the direction D6.

The X-ray imaging apparatus 1 may include a host device that controls the overall operation of the X-ray imaging apparatus 1. As an example, the host device may include a workstation 300 as shown in FIG. 1. The workstation 300 may be located in a space that is separated from a space where the THU 10 is placed by a shielding wall B. Also, as another example, the workstation 300 may be implemented as a tablet PC, a laptop computer, and a mobile device such as a smartphone.

The workstation 300 may include a display 340 that displays an X-ray image, a screen for guiding an input of a control command, a variety of setting information related to the X-ray imaging apparatus 1, and the like, and an input interface 350 that receives various kinds of control commands related to X-ray imaging from a user as an input.

The display 340 may include one of display panels such as a cathode ray tube (CRT), a digital light processing (DLP) panel, a plasma display panel, a liquid crystal display (LCD) panel, an electro luminescence (EL) panel, an electrophoretic display (EPD) panel, an electrochromic display (ECD) panel, a light emitting diode (LED) panel, and an organic light emitting diode (OLED) panel, but is not limited thereto.

The input interface 350 may be implemented as an input device such as a keyboard, a mouse, a trackball, a jog shuttle, and a touch pad. The input interface 350 may be implemented as a touch pad. When the input interface 350 is disposed on the front of the display 340, the input interface 350 may be combined with the display 340 to form a touch screen.

The X-ray detector 200 may be mounted on the detector mounting unit 21a of the imaging stand 21 or the detector mounting unit 22a of the imaging table 22.

Also, one X-ray detector may be selectively used by a plurality of X-ray imaging apparatuses, and one X-ray imaging apparatus may selectively use one of a plurality of X-ray detectors.

Accordingly, a task of pairing an X-ray detector to be used for imaging with a workstation is performed before taking an X-ray image.

An error may be caused by a user directly entering information for pairing to the workstation, and the user's work load may be increased. Accordingly, the X-ray imaging apparatus according to an example embodiment may use a mobile device to simply and accurately pair an X-ray detector with a workstation, thus reducing a possibility of an error and a user's work load.

The control panel 80 provided at the THU 10 may include an input interface 85 (see FIG. 10A) that receives a control command of the user as an input and a display 84 (see FIG. 10A) that displays a screen for guiding input of a control command or a screen for indicating a status of the X-ray imaging apparatus 1.

The user may manipulate the control panel 80 to enter a control command for X-ray imaging or, as described below, to enter a control command for pairing with the X-ray detector 200.

The control panel 80 may deliver a control command entered by the user to the workstation 300 or may directly control the THU 10 or the X-ray detector 200 according to the entered control command. That is, the control panel 80 may perform some or all functions of the workstation 300. In this case, the control panel 80 may be included in the host device.

Figure 2A:
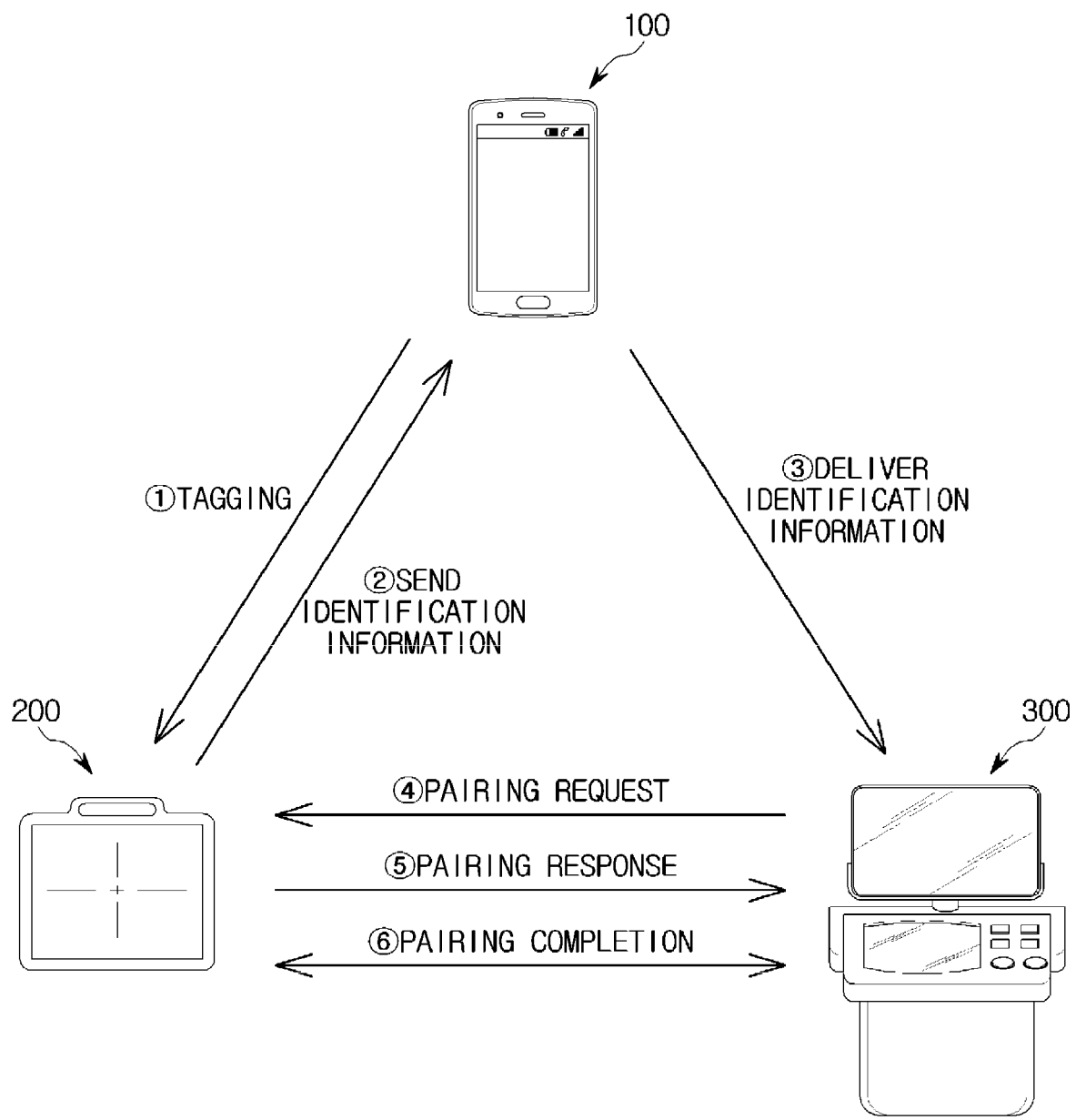
FIGS. 2A, 2B, and 2C are diagrams showing a process of pairing an X-ray detector with a workstation using a mobile device, according to an example embodiment.
Figure 2B:
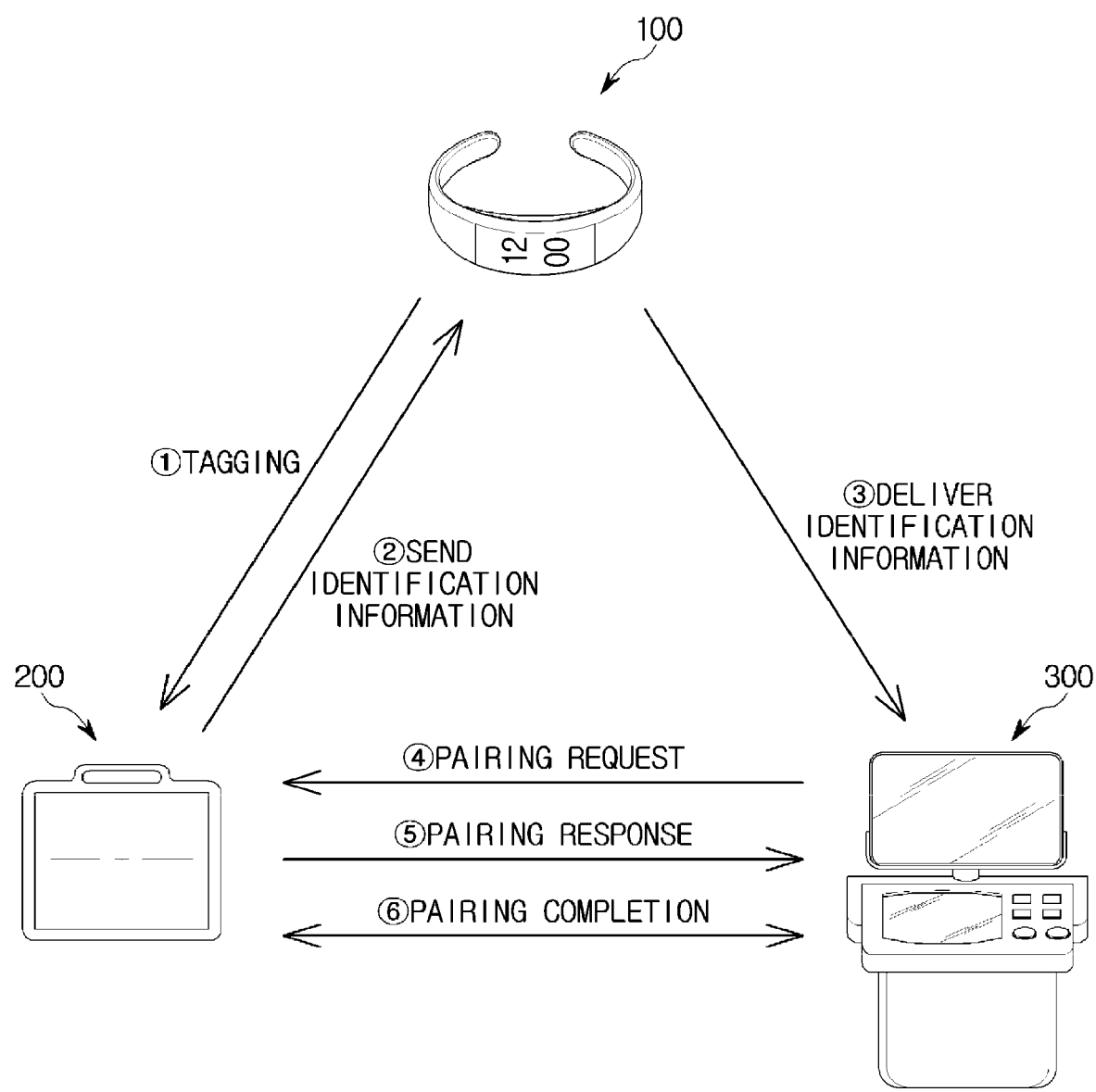
Figure 2C:
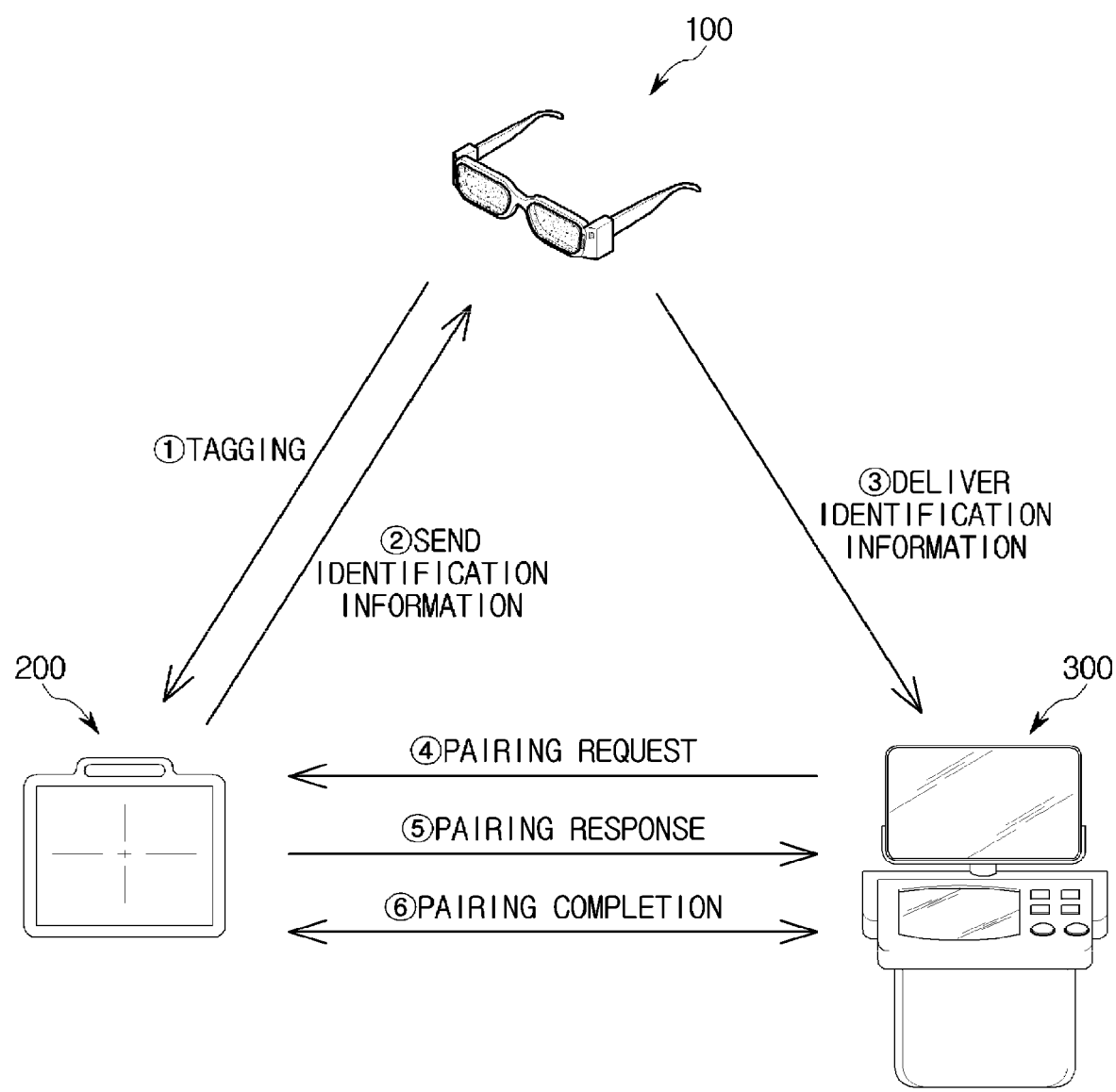
Figure 3:
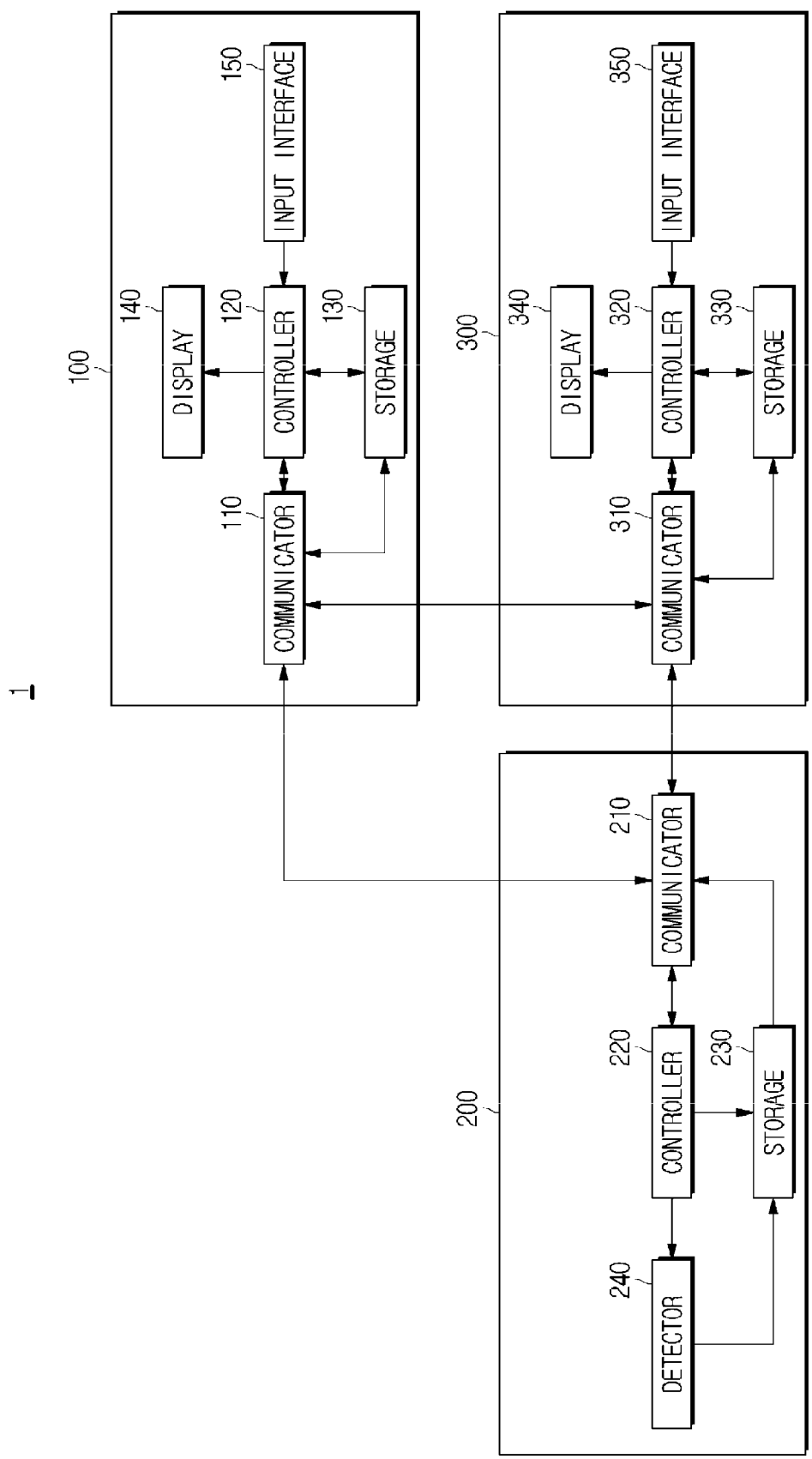
FIG. 3 is a control block diagram of an X-ray imaging apparatus according to an example embodiment.

FIGS. 2A to 2C are diagrams showing a process of pairing an X-ray detector with a workstation using a mobile device, according to an example embodiment, and FIG. 3 is a control block diagram of an X-ray imaging apparatus according to an example embodiment.

A mobile device 100 may be a portable electronic device capable of communication such as a smartphone, a smart watch, smart glasses, a tablet PC, and a PDA.

FIG. 2A shows an example in which the mobile device 100 is a smartphone, FIG. 2B shows an example in which the mobile device 100 is a smart watch, and FIG. 2C shows an example in which the mobile device 100 is smart glasses.

Referring to FIGS. 2A to 2C, when the X-ray detector 200 to be used for X-ray imaging is tagged with the mobile device 100 (①), the X-ray detector 200 sends identification information to the mobile device 100 (②). Tagging denotes bringing two devices into close proximity with each other, that is, a reference distance or less, for short-range wireless communication. A tagging operation may also include authentication by a user tagging the X-ray detector 200 to be used for X-ray imaging.

The identification information sent from the X-ray detector 200 to the mobile device 100 may include an address used for communication between the devices, such as an Internet Protocol (IP) address or a Media Access Control (MAC) address.

Also, the X-ray detector 200 may send detector information in addition to the identification information. The detector information may include information on the X-ray detector 200 such as remaining battery capacity, size, resolution, pixel size, read-out rate, and calibration information.

When the identification information is received from the X-ray detector 200, the mobile device 100 delivers the identification information to the workstation 300 (③). Also, the detector information may also be delivered together with the identification information.

When the identification information is delivered, the workstation 300 may send a pairing request to the X-ray detector 200 having the delivered identification information (④).

When the pairing request is received, the X-ray detector 200 sends a response (⑤). In this case, the X-ray detector 200 and the workstation 300 are paired and may send and receive signals to and from each other. In this example embodiment, the transmission and reception of the request and response may include transmission and reception of signals.

When the X-ray detector 200 and the workstation 300 are paired and start X-ray imaging, the X-ray detector 200 may detect an X-ray, convert the detected X-ray into X-ray data, and send the X-ray data to the workstation 300.

Also, when the X-ray detector 200 does not deliver detector information such as size, resolution, pixel size, read-out rate, and calibration information to the workstation 300 through the mobile device 100, the X-ray detector 200 may directly send the detector information after being paired with the workstation 300.

Also, the workstation 300 may send a control signal for controlling an operation of the X-ray detector 200 to the X-ray detector 200.

When the control panel 80 of the THU 10 is included in the host device, the X-ray detector 200 may send the identification information of the X-ray detector 200 to the control panel 80 rather than the workstation 300, and the control panel 80 may send a pairing request to the X-ray detector 200 having the sent identification information, thus enabling the control panel 80 and the X-ray detector 200 to be paired as shown in FIGS. 2A to 2C.

Referring to FIG. 3, the mobile device 100 according to an example embodiment may include a communicator 110, a controller 120, a storage 130, a display 140, and an input interface 150.

The communicator 110 may receive identification information from the X-ray detector 200 and may send the received identification information to the workstation 300.

The communicator 110 may include at least one wireless communication module. When the communicator 110 communicates with the X-ray detector 200 or when the communicator 110 communicates with the workstation 300, different types of communication modules or the same type of communication module may be used. The communicator 110 will be described below in detail.

The display 140 may display a screen for informing a user that the mobile device 100 has been connected with the X-ray detector 200, and the input interface 150 may receive a control command of the user as an input.

The controller 120 controls an operation of the mobile device 100. The controller 120 may control the communicator 110 to send detector information to the workstation 300 or control the display 140 to display a connection screen or the detector information.

The controller 120 may include a memory that stores a program for performing an operation that has been described or will be described and a processor that executes the program stored in the memory.

The controller 120 may include a plurality of processors or a plurality of memories depending on performed operations or processor capacity.

Also, the controller 120 may be physically separated from other elements such as the communicator 110 or the display 140 or may be integrated into a single chip.

The storage 130 may be a non-volatile memory or a volatile memory. Data temporarily needed may be stored in the volatile memory, and data needed until a deletion command is input may be stored in the non-volatile memory. For example, the identification information of the X-ray detector 200 or the identification information of the workstation 300 may be stored in the non-volatile memory and used when needed.

The storage 130 may share the memory with the controller 120. That is, a program executed by the processor of the controller 120 may be stored in the memory of the storage 130.

The mobile device 100 may be sold as an element of the X-ray imaging apparatus 1. A user may install a program for executing the above-described operation and an operation to be described below in another mobile device carried by the user. Accordingly, the mobile device 100 may or may not be an element of the X-ray imaging apparatus 1.

The X-ray detector 200 according to an example embodiment includes a communicator 210, a controller 220, a storage 230, and a detector 240.

The communicator 210 may send detector information by communicating with the mobile device 100, receive a pairing request by communicating with the workstation 300, and send X-ray data to the workstation 300 in response to the pairing request after pairing.

The communicator 210 may include at least one wireless communication module. When the communicator 210 communicates with the mobile device 100 or when the communicator 110 communicates with the workstation 300, different types of communication modules or the same type of communication module may be used. The communicator 210 will be described below in detail.

The storage 230 may be a non-volatile memory or a volatile memory. For example, the identification information of the X-ray detector 200 or the identification information of the workstation 300 may be stored in the non-volatile memory and used when needed.

Also, the storage 230 may temporarily or non-temporarily store X-ray data acquired by the detector 240.

The controller 220 may control the communicator 210 and the detector 240.

For example, when the communicator 210 is tagged by the mobile device 100, the controller 220 may control the communicator 210 to send identification information to the mobile device 100. When a pairing request is received from the workstation 300, the controller 220 may control the communicator 210 to send detector information to the workstation 300. Also, after the detector 240 detects an X-ray, the controller 220 may control the communicator 210 to send X-ray data to the workstation 300.

Also, the controller 220 may activate the detector 240. When an X-ray is incident on the detector 240, the controller 220 may control the detector 240 to detect the X-ray and convert the detected X-ray into an electric signal.

Figure 4:
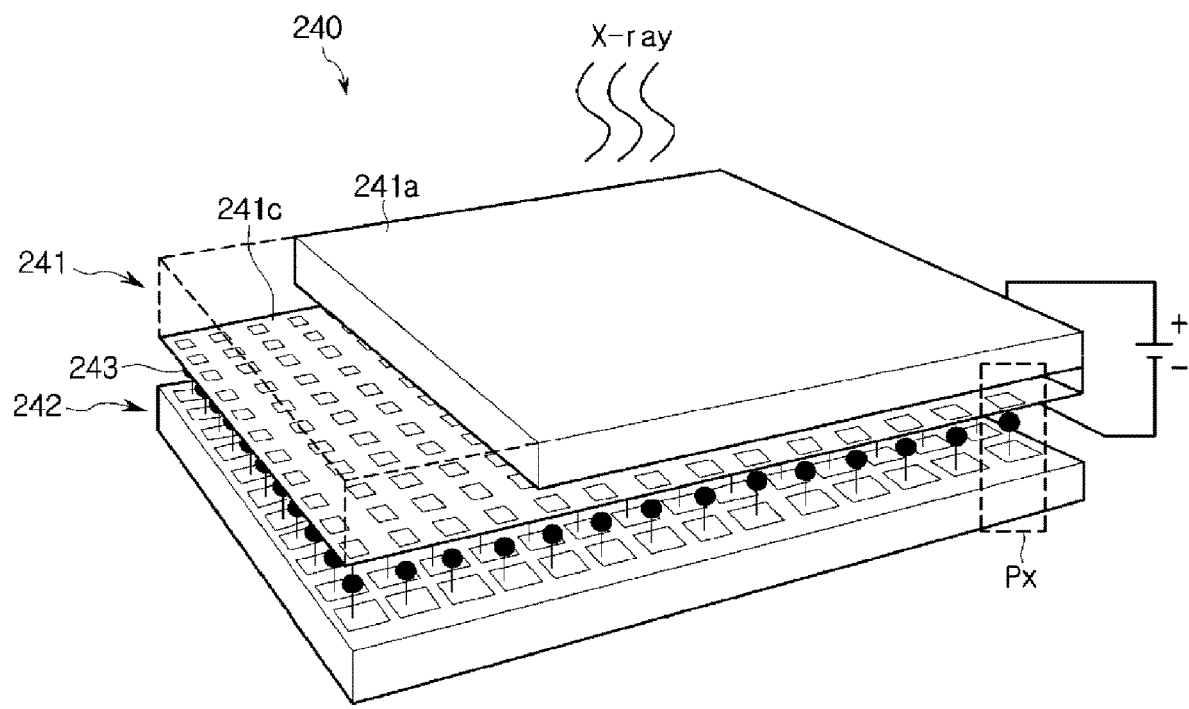
FIG. 4 is a diagram showing a configuration of a detector of an X-ray detector, according to an example embodiment.

FIG. 4 is a diagram showing a configuration of a detector of an X-ray detector, according to an example embodiment.

The detector 240 may include a light receiving device 241 that detects an X-ray and generates an electrical signal and a read-out circuit 242 that reads out the generated electrical signal. Hereinafter, the electric signal that is read out and output by the read-out circuit 242 will be referred to as X-ray data.

The light receiving device 241 may be made with a single crystal semiconductor material to ensure high resolution, high response speed, and a high dynamic area even under conditions of low energy and a small dose of X-rays. The single crystal semiconductor material may be Ge, CdTe, CdZnTe, or GaAs.

The light receiving device 241 may be in the form of a PIN photodiode. The PIN photodiode is fabricated by bonding a p-type semiconductor substrate 241c of a 2D array structure under an n-type semiconductor substrate 241a with high resistance.

The read-out circuit 242, which is fabricated according to a complementary metal-oxide semiconductor (CMOS) process, is in the form of a 2D array structure and may be combined with the p-type semiconductor substrate 241c of the light receiving device 241 in units of pixels. In this case, a flip-chip bonding (FCB) method of forming bumps 243 with solder (PbSn), indium (In), or the like and then reflowing, applying heat, and applying pressure may be used as the combining method.

As described above, the X-ray detector 200 may be mounted on the detector mounting unit 21a provided at the imaging stand 21 or mounted on the detector mounting unit 22a provided at the imaging table 22. Alternatively, the X-ray detector 200 may be used portably rather than being mounted on a mounting unit.

A structure of the above-described X-ray detector is an example that may be applied to the X-ray imaging apparatus 1. An example of the X-ray imaging apparatus 1 or an example of the X-ray detector 200 is not limited to the structure.

For example, the X-ray detector 200 may have various structures depending on a material configuration method, a method of converting a detected X-ray into an electric signal, and a method of acquiring an electric signal. The above-described structure is an example of the detector 240 included in the X-ray detector 200. A structure of the detector 240 is not limited to the above-described example.

The X-ray detector 200 may include in the X-ray imaging apparatus 1 and sold or may be sold separately from the X-ray imaging apparatus 1 and then used after being registered. Accordingly, the X-ray imaging apparatus 1 may or may not include the X-ray detector 200.

Referring to FIG. 3 again, the workstation 300 includes a communicator 310, a controller 320, a storage 330, a display 340, and an input interface 350.

The communicator 310 may receive the identification information of the X-ray detector 200 from the mobile device 100 and may send a pairing request to the X-ray detector 200 having the received identification information. Also, after the workstation 300 is paired with the X-ray detector 200, the communicator 310 may receive X-ray data from the X-ray detector 200.

When the communicator 310 receives the identification information of the X-ray detector 200 from the mobile device 100, the controller 320 may control the communicator 310 to send the pairing request to the X-ray detector 200 having the received identification information.

Also, the controller 320 may process X-ray data received from the X-ray detector 200 to generate an X-ray image from which a lesion may be identified.

The storage 330 may store the identification information of the X-ray detector 200 received from the mobile device 100. Also, the storage 330 may store the X-ray data received from the X-ray detector 200, the X-ray image generated by processing the X-ray data, and the like.

Figure 5:
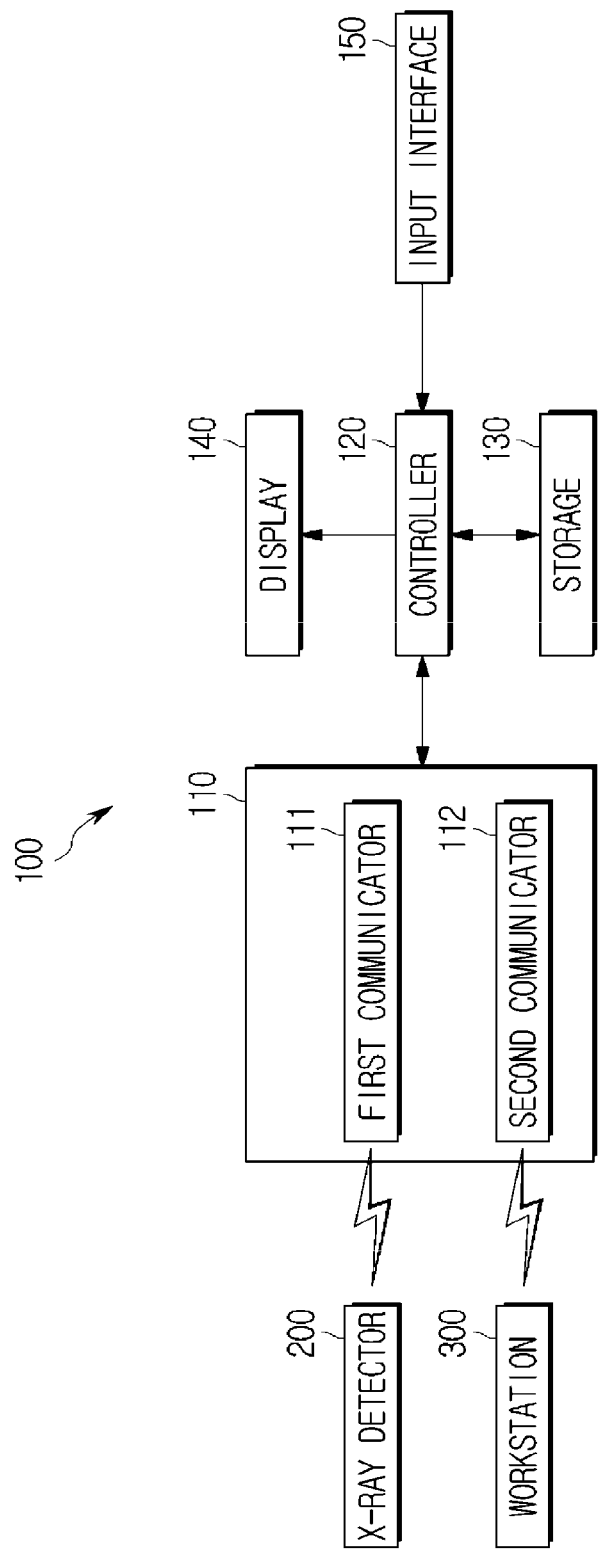
FIG. 5 is a control block diagram of a mobile device including different communication modules, according to an example embodiment.
Figure 6:
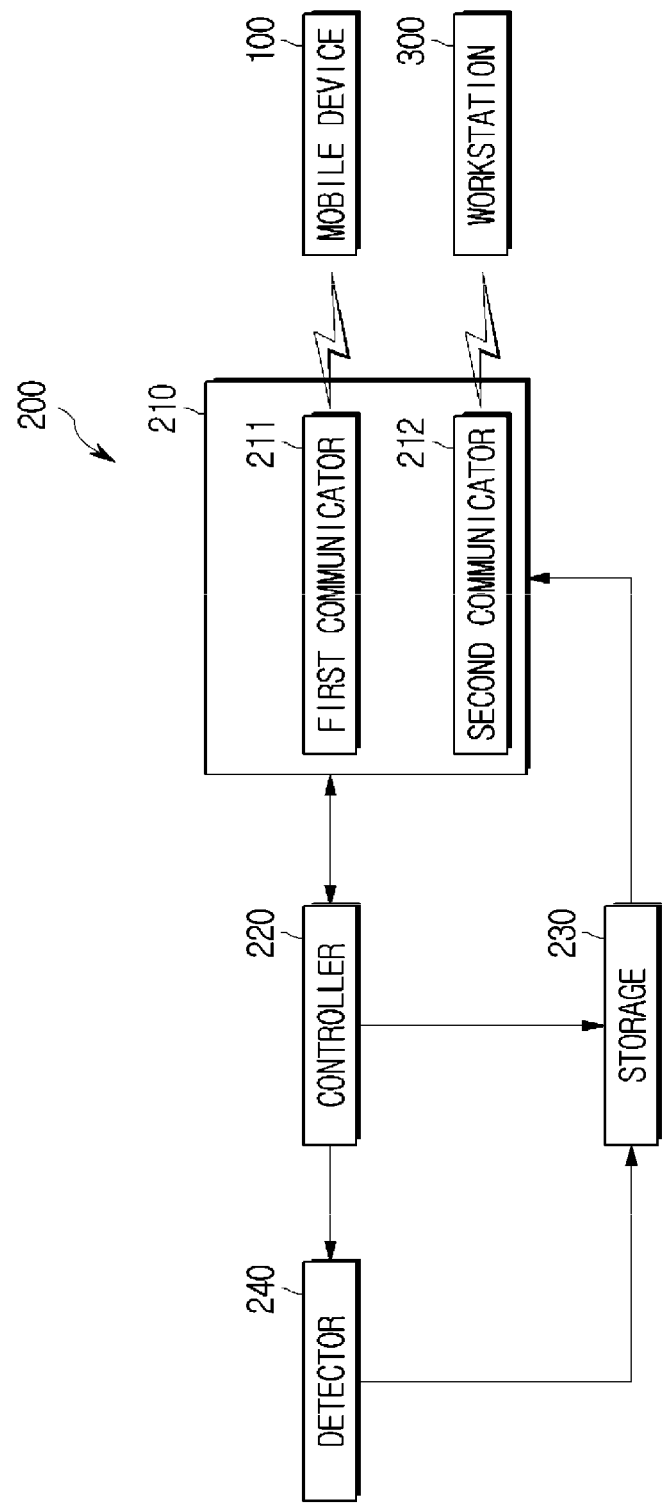
FIG. 6 is a control block diagram of an X-ray detector including different communication modules, according to an example embodiment.
Figure 7B:
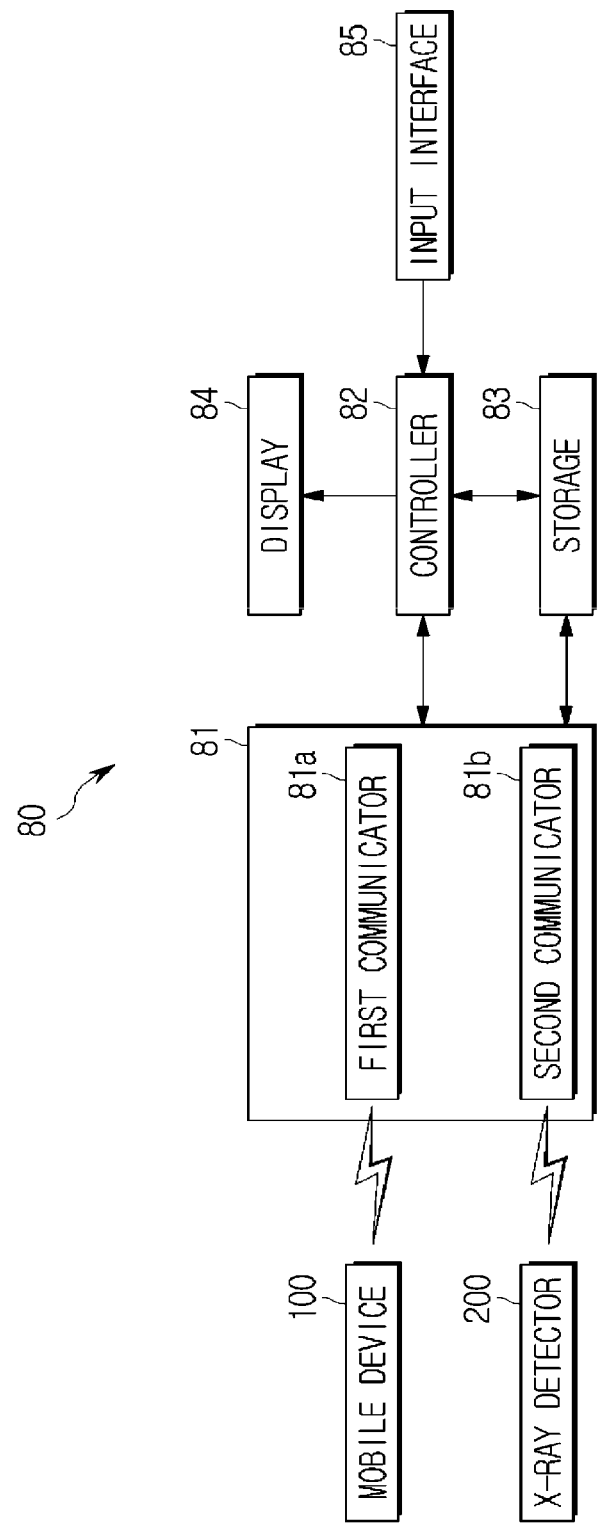
FIG. 7B is a control block diagram of a control panel capable of being paired with an X-ray detector, according to an example embodiment.

FIG. 5 is a control block diagram of a mobile device including different communication modules, according to an example embodiment, FIG. 6 is a control block diagram of an X-ray detector including different communication modules, according to an example embodiment, FIG. 7A is a control block diagram of a workstation including different communication modules, according to an example embodiment, and FIG. 7B is a control block diagram of a control panel capable of being paired with an X-ray detector, according to an example embodiment.

Referring to FIG. 5, the communicator 110 of the mobile device 100 may include a first communicator 111 that communicates with the X-ray detector 200 and a second communicator 112 that communicates with the workstation 300.

Referring to FIG. 6, the communicator 210 of the X-ray detector 200 may include a first communicator 211 that communicates with the mobile device 100 and a second communicator 212 that communicates with the workstation 300.

Referring to FIG. 7A, the communicator 310 of the workstation 300 may include a first communicator 311 that communicates with the mobile device 100 and a second communicator 312 that communicates with the X-ray detector 200.

Also, when the control panel 80 is included in a host device so that the X-ray detector 200 and the control panel 80 may be paired, the control panel 80 may include a communicator 81 that communicates with the mobile device 100 and the X-ray detector 200, and a controller 82 may control an operation of performing pairing with the X-ray detector 200, as shown in FIG. 7B.

Also, the storage 83 may store the identification information of the X-ray detector 200 that is received from the mobile device 100.

Also, the communicator 81 may include a first communicator 81a that communicates with the mobile device 100 and a second communicator 81b that communicates with the X-ray detector 200.

In the following example embodiment, pairing between the workstation 300 and the X-ray detector 200 will be described in detail. The description can be equally applicable to pairing between the X-ray detector 200 and the control panel 80 of the THU 10.

The mobile device 100 and the X-ray detector 200, the mobile device 100 and the workstation 300, or the X-ray detector 200 and the workstation 300 may be mutually connected through short-range wireless communication. Examples of short-range communication technology that may be applied to this example embodiment include Wireless LAN, Wi-Fi, Bluetooth, ZigBee, Wi-Fi Direct (WFD), ultra wideband (UWB), Infrared Data Association (IrDA), Bluetooth Low Energy (BLE), and Near Field Communication (NFC).

For example, the mobile device 100 and the X-ray detector 200 may perform communication by employing one of short-range wireless communication methods in which data may be sent or received through tagging, such as an NFC method and a radio frequency identification (RFID) method.

In this case, the first communicator 111 of the mobile device 100 may include any one or any combination of devices capable of receiving or reading signals over a short distance, such as an NFC module and an RFID reader, and the first communicator 211 of the X-ray detector 200 may include any one or any combination of devices capable of sending or reading signals over a short distance, such as an NFC module and an RFID tag.

Here, the modules or the tags that are included in the first communicators 111 and 211 correspond to each other. That is, when the first communicator 111 of the mobile device 100 includes an NFC module, the first communicator 211 of the X-ray detector 200 also includes an NFC module. When the first communicator 111 of the mobile device 100 includes an RFID reader, the first communicator 211 of the X-ray detector 200 includes an RFID tag.

NFC communication is a non-contact communication technology for sending and receiving radio data over a short distance of 10 cm or less according to the NFC standard, and uses a frequency band of 13.56 MHz.

NFC communication enables bi-directional communication. That is, the NFC module may perform functions of both an NFC reader and an NFC tag. Accordingly, the NFC module included in the first communicator 111 of the mobile device 100 may send data to the NFC module included in the first communicator 211 of the X-ray detector 200.

The NFC module may include an antenna that sends and receives signals, a modulator that modulates a signal to be sent through the antenna, and a demodulator that demodulates a signal received through the antenna. However, the NFC module included in the first communicator 211 of the X-ray detector 200 may include only an NFC tag.

The identification information of the X-ray detector 200 may be sent to the mobile device 100 through the NFC module. The detector information such as size, resolution, pixel size, read-out rate, and calibration information of the X-ray detector 200 may be further sent.

When there is no need for the mobile device 100 to send signals to the X-ray detector 200, the first communicator 211 of the X-ray detector 200 may include only an NFC tag in which the identification information has been recorded.

RFID communication is a non-contact communication technology for sending and receiving radio data over a distance of 1 to 2 m, and uses a frequency band of 900 MHz.

Because RFID communication supports only a read function, unlike NFC communication, an RFID reader included in the first communicator 111 of the mobile device 100 reads information recorded in an RFID tag included in the second communicator 212 of the X-ray detector 200 when the mobile device 100 and the X-ray detector 200 send and receive data using RFID communication.

Accordingly, the identification information of the X-ray detector 200 may be recorded in the RFID tag included in the second communicator 212 of the X-ray detector 200, and the detector information such as size, resolution, pixel size, read-out rate, and calibration information of the X-ray detector 200 may also be recorded.

However, the NFC and RFID methods are examples of communication methods used by the mobile device 100 and the X-ray detector 200 to send and receive signals. Signals may be sent and received using other communication methods.

Also, the mobile device 100 and the workstation 300 may send and receive data through short-range wireless communication.

For example, the second communicator 112 of the mobile device 100 may include any one or any combination of devices capable of sending signals a short distance, such as an NFC module, a Bluetooth module, and a beacon.

Also, the first communicator 311 of the workstation 300 may include any one or any combination of devices capable of receiving signals over a short distance, such as an NFC module, a Bluetooth module, and a BLE module.

Here, a module included in the first communicator 311 of the workstation 300 corresponds to that of the second communicator 112 of the mobile device 100. That is, when the second communicator 112 of the mobile device 100 includes an NFC module, the first communicator 311 of the workstation 300 also includes an NFC module. When the second communicator 112 of the mobile device 100 includes a Bluetooth module, the first communicator 311 of the workstation 300 also includes a Bluetooth module. When the second communicator 112 of the mobile device 100 includes a beacon, the first communicator 311 of the workstation 300 includes a BLE module.

An example in which the second communicator 112 of the mobile device 100 includes a beacon and the first communicator 311 of the workstation 300 includes a BLE module will be described in detail.

The beacon is a short-range wireless communication device based on a Bluetooth 4.0 or BLE protocol, which may send signals to a BLE module that is located within about 50 m to 70 m without a separate pairing step.

The beacon transmits identification information (ID) of the X-ray detector 200 a range of about 50 m to 70 m. The BLE module of the workstation 300 that has entered the range recognizes the beacon and receives the identification information transmitted by the beacon.

The BLE module does not have a large influence on a battery capacity although a Bluetooth function is always turned on because the BLE module operates with low power. Accordingly, when a user tags the X-ray detector 200 with the mobile device 100 and moves to a position within a range of the workstation 300 in a state in which the BLE module of the workstation 300 is always turned on, the workstation 300 may receive a beacon signal transmitted by the mobile device 100 and acquire the identification information of the X-ray detector 200 included in the beacon signal.

Here, the mobile device 100 may deliver the identification information of the X-ray detector received by the first communicator 111 to the workstation 300 through the second communicator 112.

Likewise, the BLE communication method is also an example of a communication method used by the mobile device 100 and the workstation to send and receive signals. Signals may be sent and received using other communication methods.

When the first communicator 311 of the workstation 300 acquires the identification information of the X-ray detector 200 from the mobile device 100, the second communicator 312 of the workstation 300 sends a pairing request to the X-ray detector 200.

The second communicator 212 of the X-ray detector 200 sends a response to the second communicator 312 of the workstation 300 when the pairing request is received, and the pairing between the X-ray detector 200 and the workstation 300 is completed. Here, the completion of the pairing means that the X-ray detector 200 and the workstation 300 may send and receive signals.

For example, the X-ray detector 200 and the workstation 300 may communicate through WFD. In this case, the second communicator 212 of the X-ray detector 200 and the second communicator 312 of the workstation 300 may each include a WFD module.

Also, the communicator 310 of the workstation 300 may further include a wireless communication module for sending and receiving signals to and from any one or any combination of a base station of a mobile communication network, a distant electronic device, and a server such as a picture archiving and communication system (PACS).

An example in which the communication method between the mobile device 100 and the X-ray detector 200, the communication method between the mobile device 100 and the workstation 300, and the communication method between the workstation 300 and the X-ray detector 200 are different from each other has been described above, but example embodiments are not limited thereto. Accordingly, some or all of the methods may employ the same communication method.

When the X-ray detector 200 and the workstation 300 are paired, the X-ray detector 200 may send detector information to the workstation 300, and the workstation 300 may send a control signal for controlling the X-ray detector 200.

When X-ray imaging is started, the X-ray detector 200 detects an X-ray and sends X-ray data acquired from the detected X-ray. The controller 320 of the workstation 300 may generate an X-ray image from which a lesion can be identified by processing the X-ray data using the detector information. The display 340 may display the generated X-ray image. The input interface 350 may receive a control command associated with X-ray imaging and X-ray image generation from a user as an input.

The storage 330 may temporarily or non-temporarily store identification information, detector information, X-ray data, and an X-ray image of the X-ray detector 200.

Also, the communicator 310 may send the generated X-ray image to a PACS or other terminals. In this case, the above-described wireless communication module may be used.

Figure 8A:
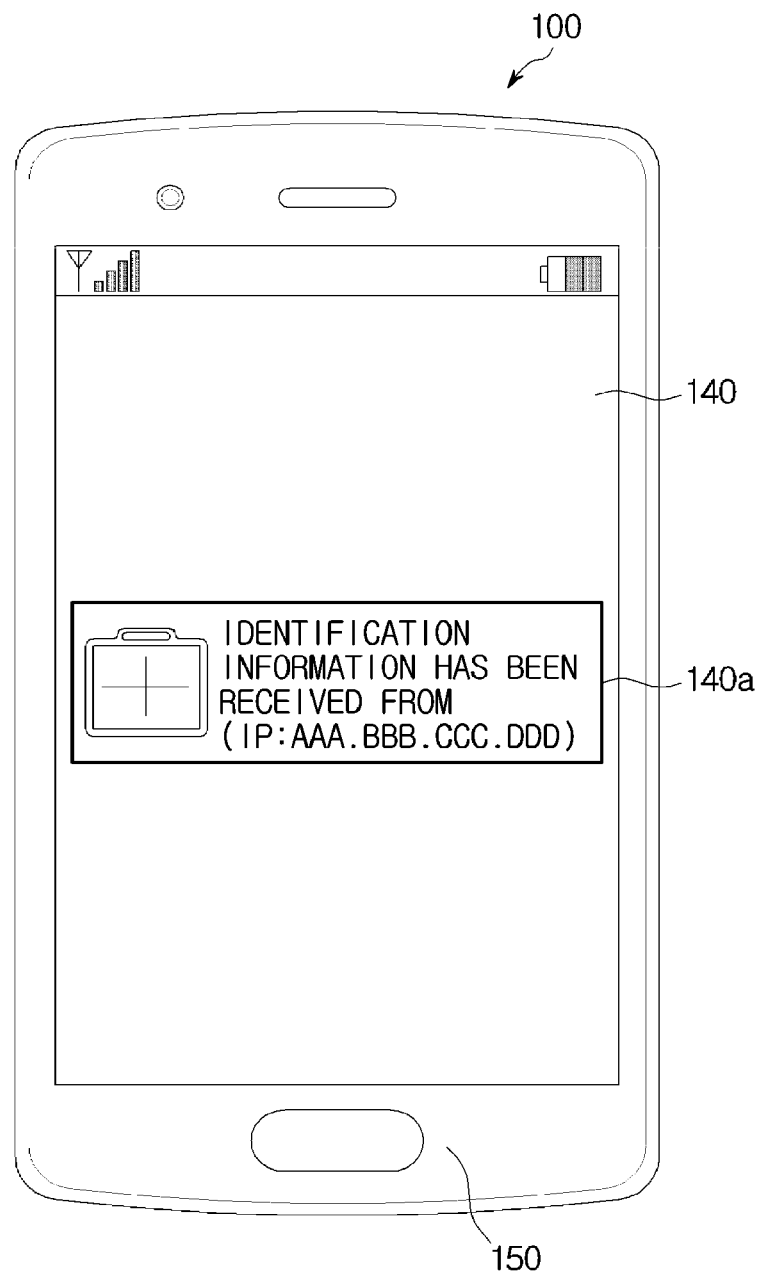
FIGS. 8A, 8B, and 8C are diagrams showing examples of a screen that may be displayed when an X-ray detector is tagged with a mobile device, according to an example embodiment.
Figure 8B:
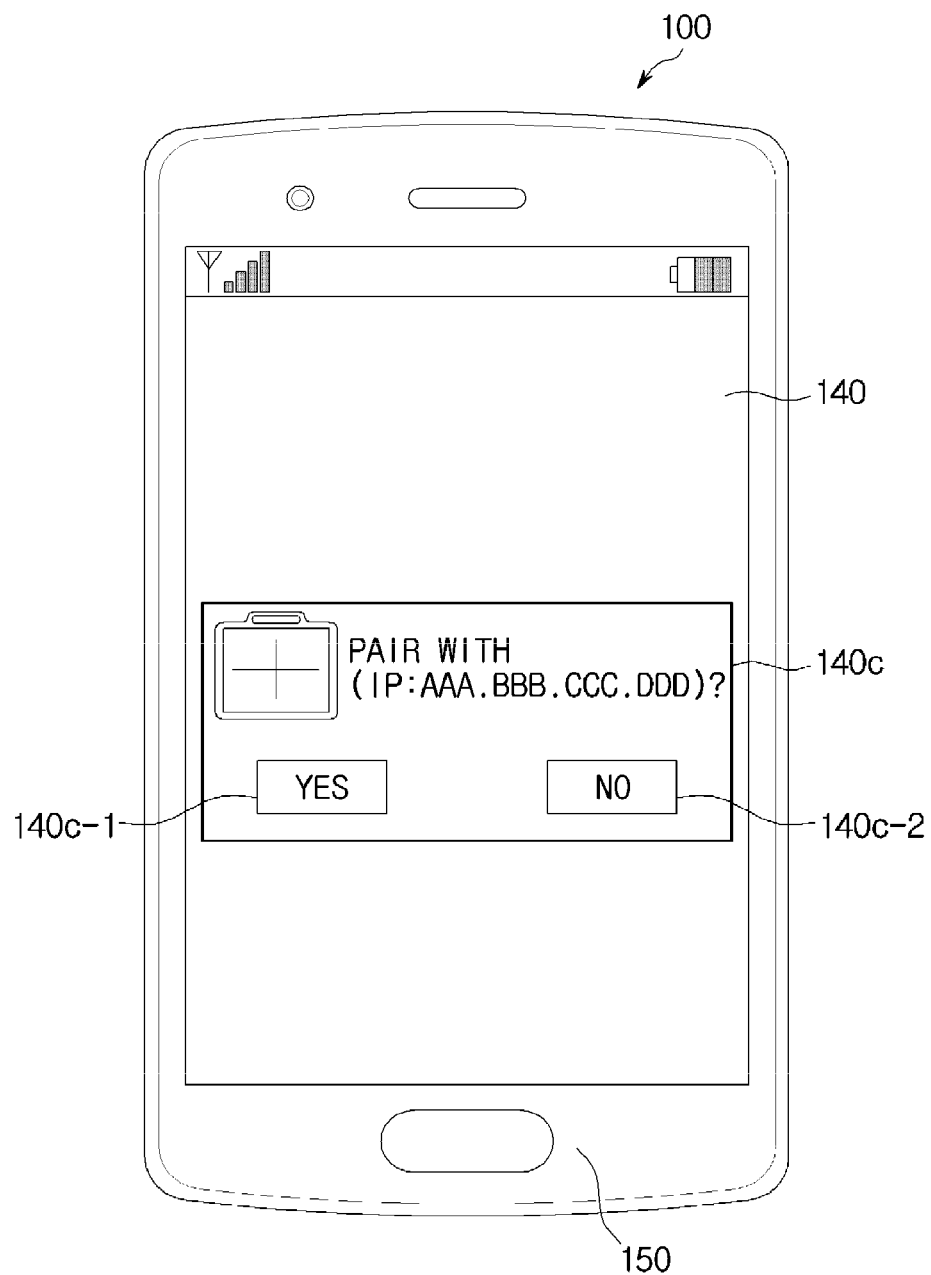
Figure 8C:
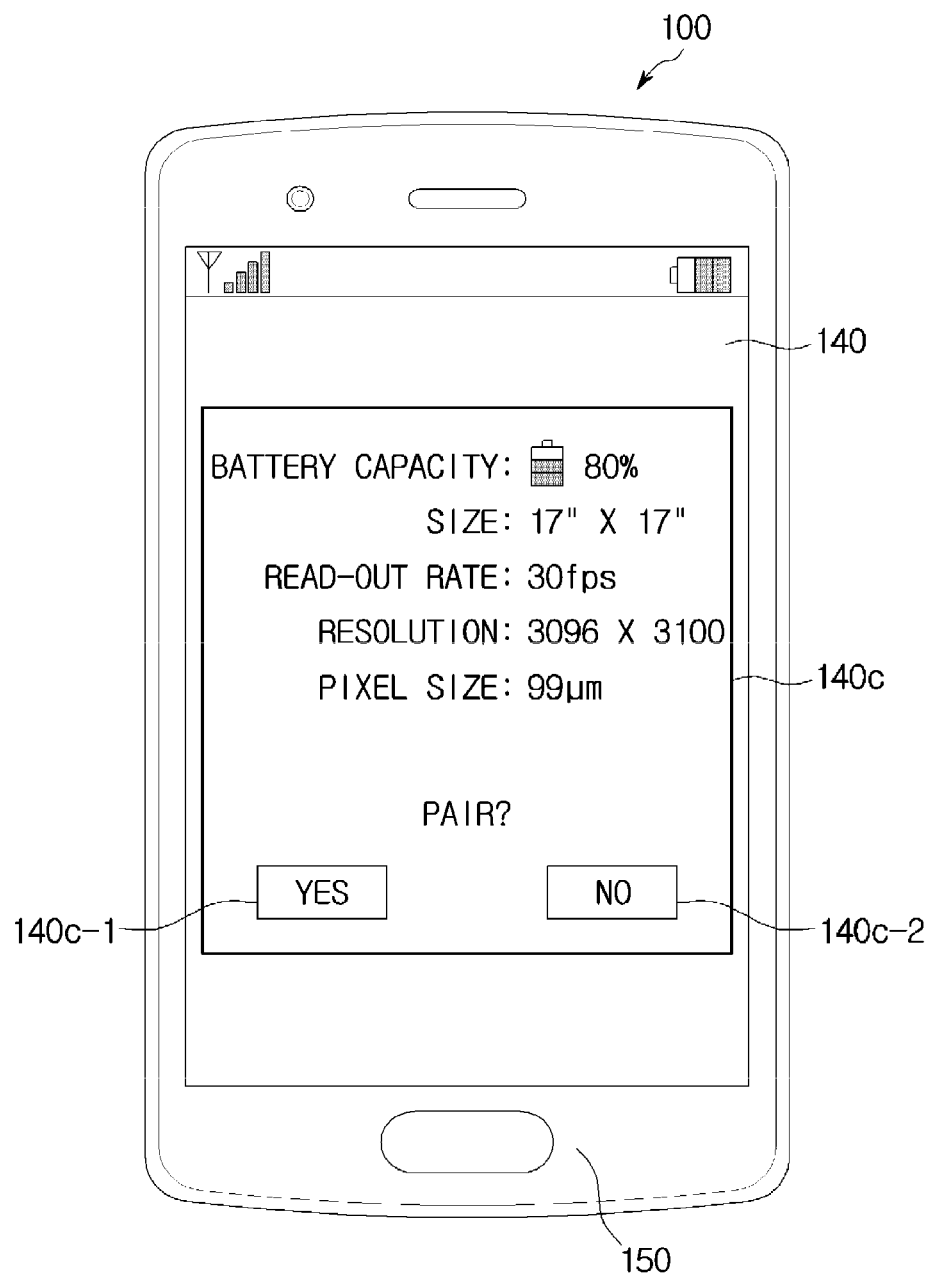
Figure 9B:
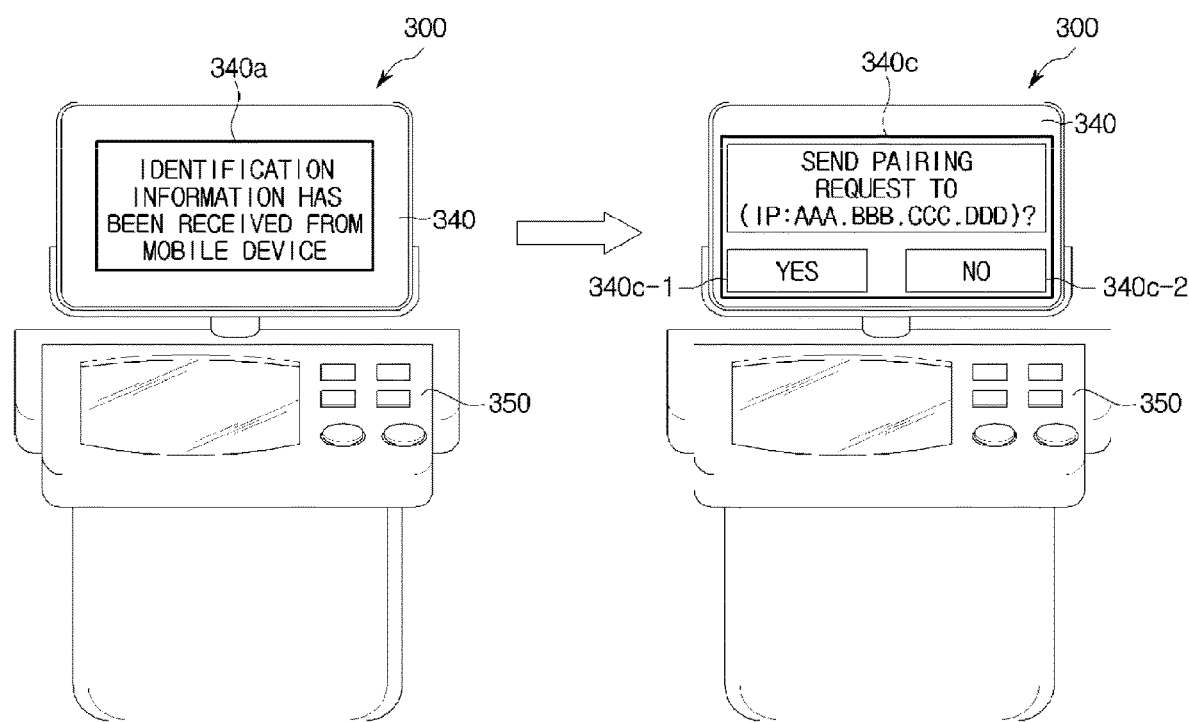
Figure 10A:
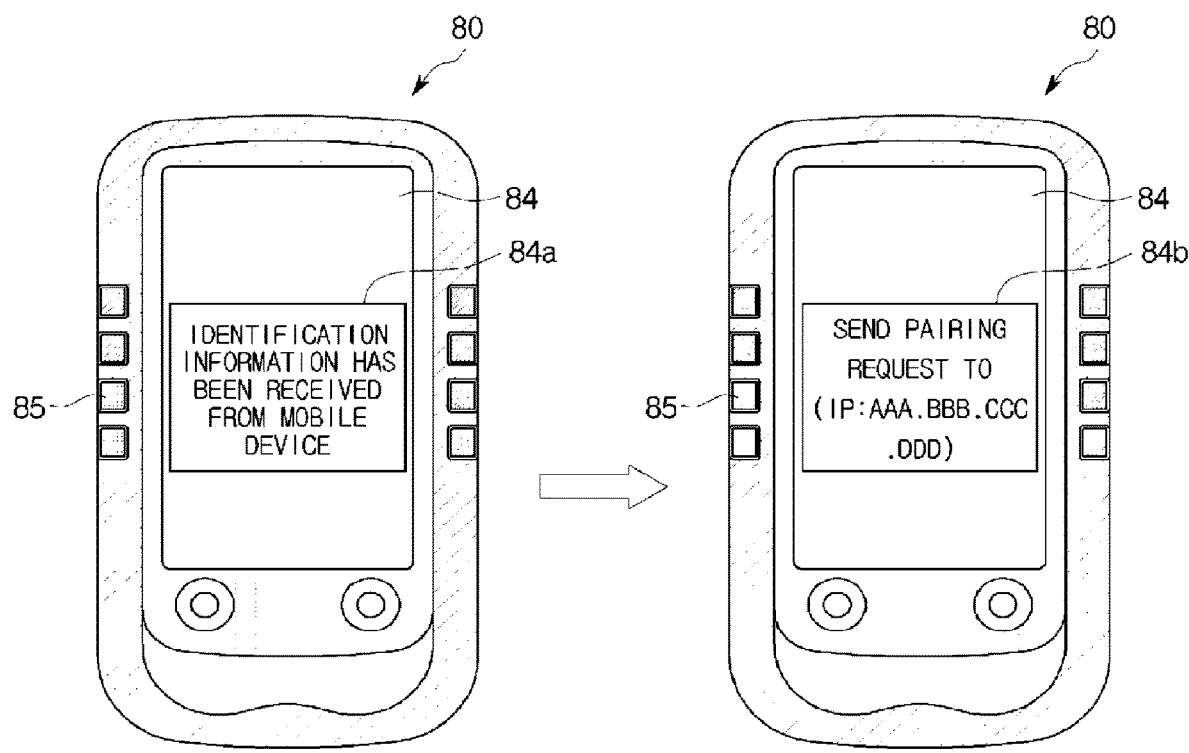
FIGS. 10A and 10B are diagrams showing examples of a screen that may be displayed when a tube head unit receives identification information of an X-ray detector from a mobile device, according to an example embodiment.
Figure 10B:
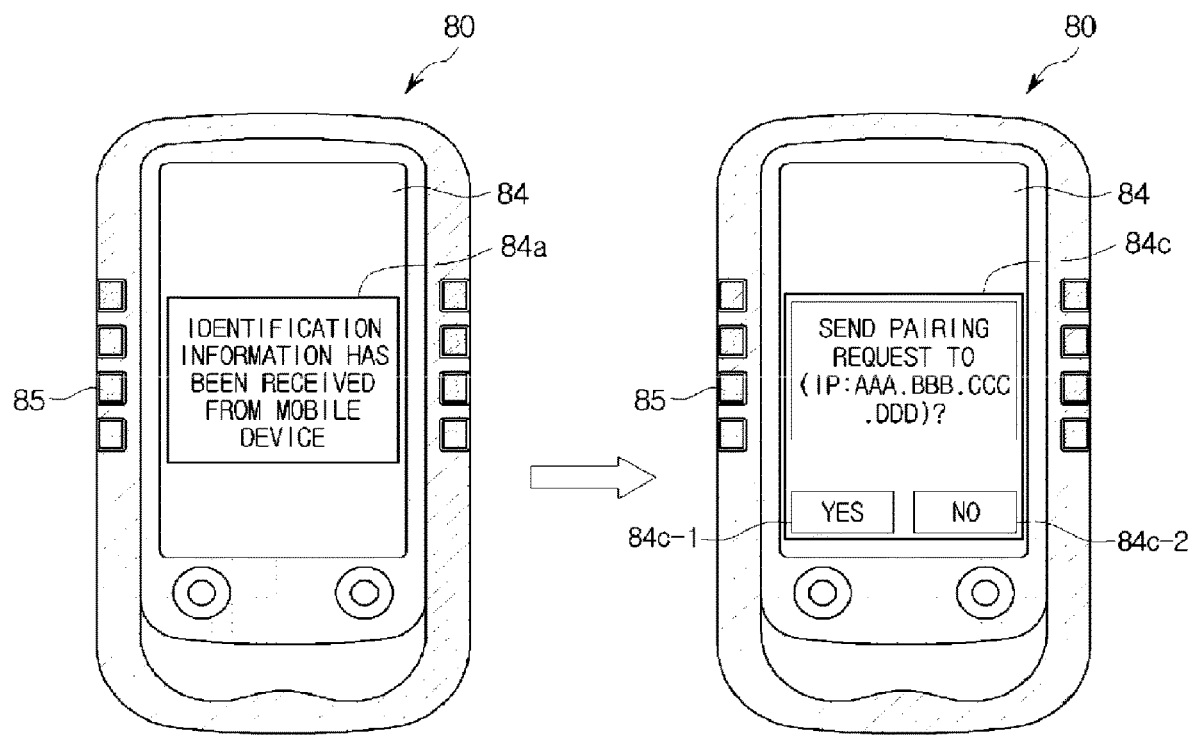

FIGS. 8A, 8B, and 8C are diagrams showing examples of a screen that may be displayed when an X-ray detector is tagged with a mobile device, according to an example embodiment, FIGS. 9A and 9B are diagrams showing examples of a screen that may be displayed when a workstation receives identification information of an X-ray detector from a mobile device, according to an example embodiment, and FIGS. 10A and 10B are diagrams showing examples of a screen that may be displayed when a THU receives identification information of an X-ray detector from a mobile device, according to an example embodiment.

As described above, when the X-ray detector 200 is tagged with the mobile device 100, the identification information of the X-ray detector 200 is sent to the mobile device 100. As shown in FIG. 8A, a reception screen 140a that informs that the identification information has been received from the X-ray detector 200 may be displayed on the display 140 of the mobile device 100, and the received identification information may also be displayed in the reception screen 140a.

Alternatively, recognition identification information for facilitating recognition of the X-ray detector by a user, such as a model name of the X-ray detector or a name set by the user may be displayed rather than identification information used to perform pairing with the workstation, such as an IP address or MAC address.

The recognition identification information may be sent by the X-ray detector 200 together with the identification information for pairing or may be mapped to the identification information for pairing and prestored in the storage 130 of the mobile device 100.

The user may confirm that the identification information has been sent from the X-ray detector 200 by viewing the reception screen 140a and may move to the vicinity of the workstation 300 while carrying the mobile device 100. Alternatively, the user may not move depending on whether the X-ray detector 200 is mounted on the detector mounting unit 21a or 22a, a distance between the workstation 300 and the X-ray detector 200, and the like, and the workstation 300 and the mobile device 100 have only to be positioned in a communicable distance.

For example, assuming that the communicator 110 of the mobile device 100 includes a beacon and that the communicator 310 of the workstation 300 includes a BLE module, the identification information of the X-ray detector 200 may be acquired from the mobile device 100 as long as a user who carries the mobile device 100 is positioned within a distance of about 50 m to 70 m from the workstation 300.

Alternatively, as shown in FIG. 8B, a pairing approval screen 140c for receiving an input on whether the pairing is approved from the user may be displayed on the display 140 of the mobile device 100. When the user selects a "yes" button 140c-1, the identification information of the X-ray detector 200 may be delivered to the workstation 300. When the user selects a "no" button 140c-2, the identification information of the X-ray detector 200 may not be delivered to the workstation 300.

Alternatively, when the X-ray detector 200 sends detector information such as battery capacity, size, read-out rate, resolution, calibration information, and pixel size to the mobile device 100 in addition to its own identification information, the detector information may be displayed on the pairing approval screen 140c as shown in FIG. 8C. The user may confirm the detector information and determine whether the X-ray detector is suitable for X-ray imaging to be performed by the X-ray detector and confirm the detector information.

When the user determines to pair the X-ray detector and the workstation, the user may manipulate the input interface 150 to select the "yes" button 140c-1. When the user determines not to perform pairing, the user may manipulate the input interface 150 to select the "no" button 140c-2.

When the X-ray detector 200 sends the detector information to the mobile device 100, the mobile device 100 may deliver the detector information to the workstation 300 together with the identification information or may deliver only the identification information to the workstation 300.

When the mobile device 100 delivers the identification information received from the X-ray detector 200 to the workstation 300, a reception screen 340a that informs a user that the identification information has been received from the mobile device 100 may be displayed on the display 340 of the workstation 300 as shown on the left side of FIG. 9A.

Even when a user does not perform a separate operation, the workstation 300 may send a pairing request to the X-ray detector having the received identification information. In this case, a pairing request screen 340b that informs a user that the pairing request has been received may be displayed on the display 340. The user may recognize a current status by viewing the screens 340a and 340b displayed on the display 340.

Alternatively, as shown in FIG. 9B, before a pairing request is sent, a pairing approval screen 140c for receiving an input about whether the pairing is approved from a user may be displayed on the display 340. When the user selects a "yes" button 340c-1, the workstation 300 may send a pairing request to the X-ray detector. When the user selects a "no" button 340c-2, the workstation 300 may enter a standby state in which the workstation 300 waits for identification information from the mobile device 100 to be received rather than sending a pairing request.

FIGS. 9A and 9B show an example in which an IP address, which is identification information for pairing, is displayed on the screen 340b. However, recognition identification information may be displayed. For example, when a user wrongly performs tagging, that is, when another X-ray detector is tagged instead of an X-ray detector to be originally used, the user may confirm the wrong tagging by viewing the recognition identification information displayed on the screen 340b and selecting the "no" button 340c-2.

When the control panel 80 of the THU 10 and the X-ray detector 200 are paired, the mobile device 100 may deliver the identification information of the X-ray detector 200 to the control panel 80. In this case, as shown in FIG. 10A, a reception screen 84a that informs the user that the identification information has been received from the mobile device may be displayed on the display 84 of the control panel 80.

The control panel 80 may automatically send a pairing request to the X-ray detector 200 having the received identification information. In this case, a pairing request screen 84b that informs the user that the pairing request has been received may be displayed on the display 84. The user may recognize a current status by viewing the screens 84a and 84b displayed on the display 84.

Alternatively, as shown in FIG. 10B, a pairing approval screen 84c may be displayed on the display 84 before a pairing request is sent, thus enabling the user to select whether to send a pairing request.

When a user selects a "yes" button 84c-1, the control panel 80 may send a pairing request to an X-ray detector. When the user selects a "no" button 84c-2, the control panel 80 may wait until new identification information is received instead of sending a pairing request.

Pairing between the X-ray detector 200 and the workstation 300 or between the X-ray detector 200 and the control panel 80 may be completed only when the user approves the pairing. This will be described below with reference to FIG. 11.

Figure 11:
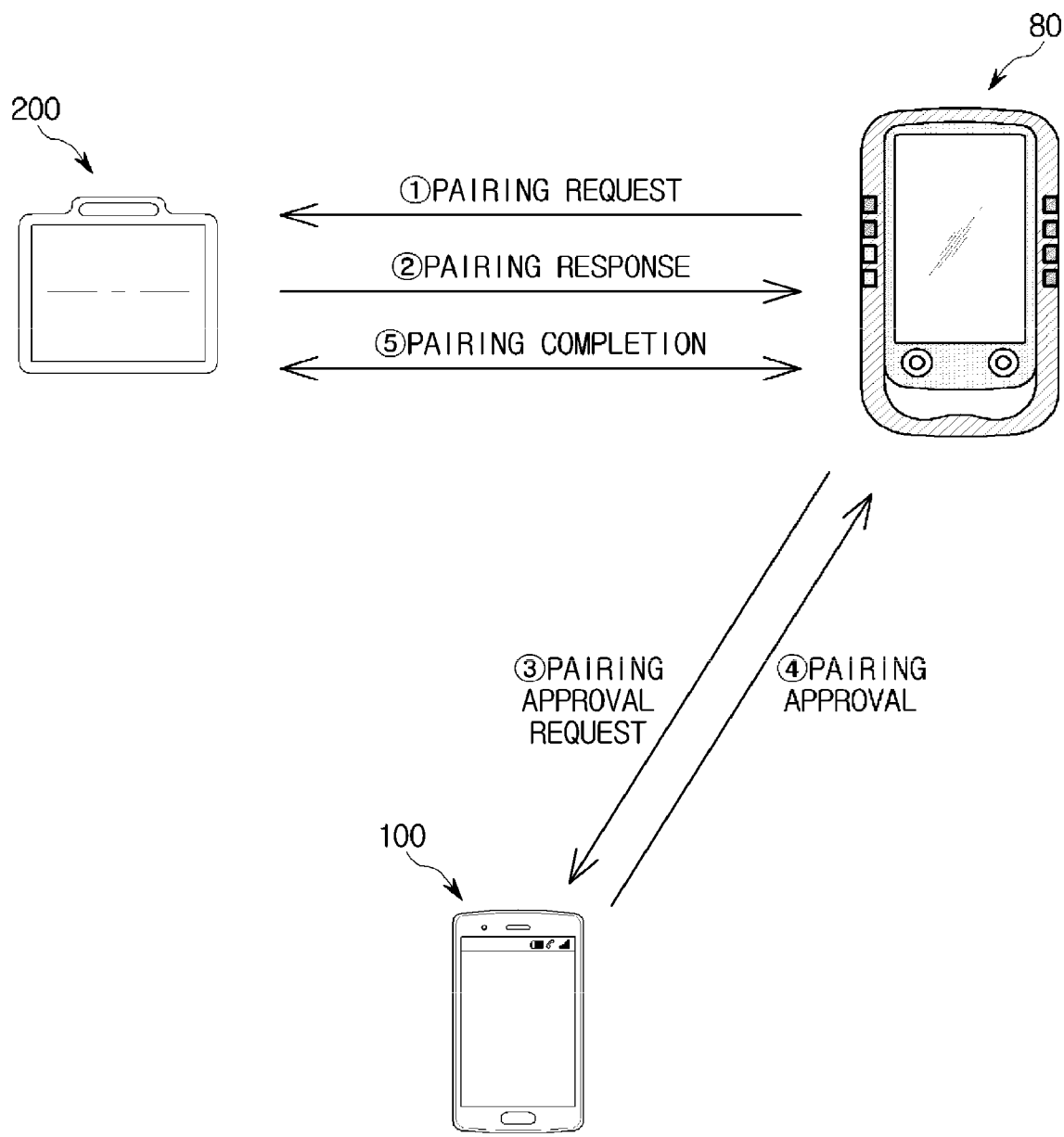
FIG. 11 is a diagram showing an example in which approval of pairing of an X-ray detector is finally received from a user, according to an example embodiment.

FIG. 11 is a diagram showing an example in which approval of pairing of an X-ray detector is finally received from a user, according to an example embodiment.

As shown in FIG. 11, the workstation 300 sends a pairing request to the X-ray detector 200 (①). When the X-ray detector 200 sends a pairing response to the workstation 300, pairing is not immediately completed (②), and the workstation 300 may send a pairing approval request to the mobile device 100 (③). This is so that final approval of the pairing between the X-ray detector 200 and the workstation 300 may be received from a user.

The mobile device 100 may display a screen such as the above-described example shown in FIG. 8B or 8C to provide the user with information regarding the X-ray detector 200 with which the workstation 300 intends to be paired. When the user inputs a pairing approval command, the mobile device 100 sends a pairing approval signal to the workstation 300 (④).

When the pairing approval signal is sent from the mobile device 100, the workstation 300 and the X-ray detector 200 are paired and may send and receive signals to and from each other (⑤).

That is, according to this example embodiment, even though a user does not input a separate command other than tagging or moving to a position within a communication distance, it is possible to automatically perform pairing between the X-ray detector 200 and a host device (a workstation or a control panel). It is also possible to prevent unintended pairing by asking the user whether to approve the pairing before the identification information of the X-ray detector 200 is delivered from the mobile device 100 to the host device, before the host device sends a pairing request to the X-ray detector 200, or after the X-ray detector 200 responds to the pairing request of the host device.

Figure 12:
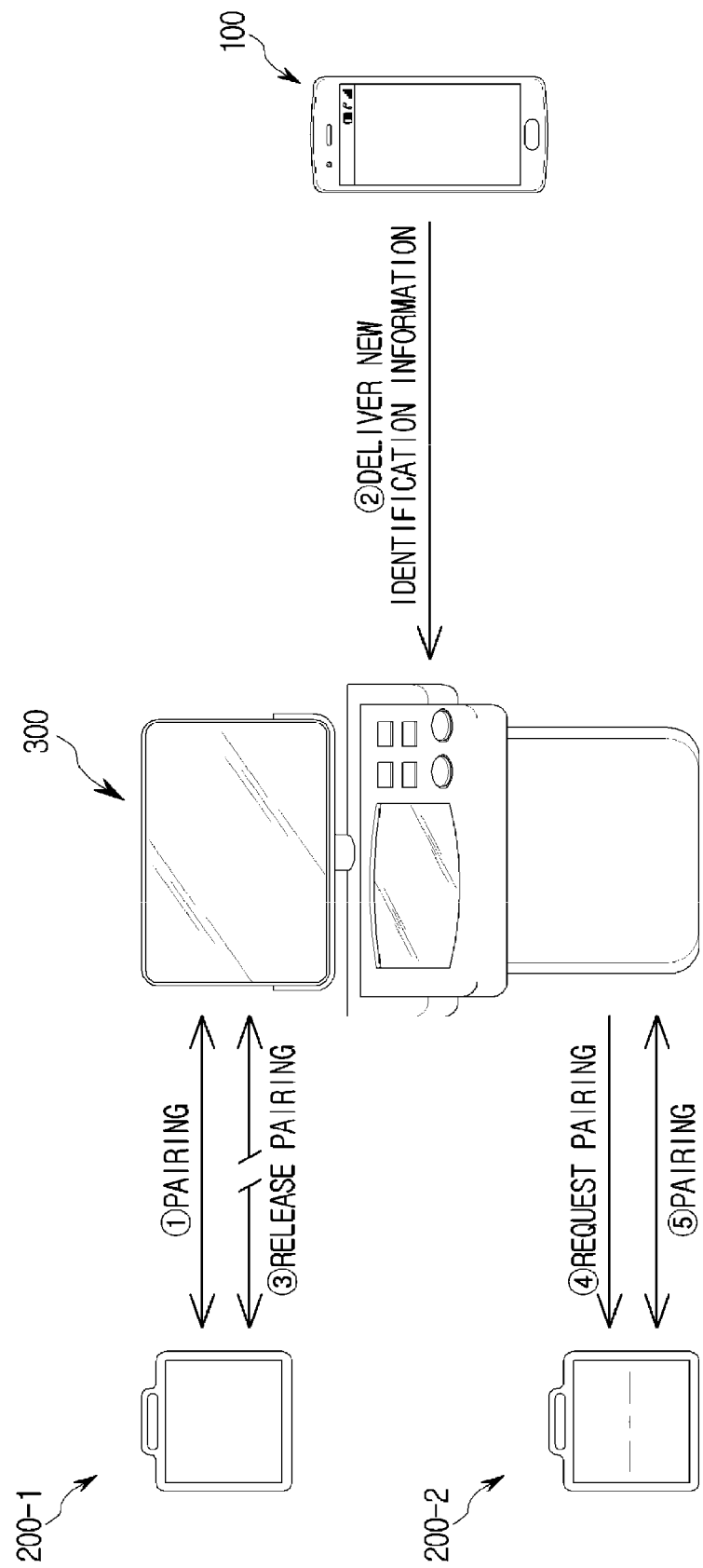
FIG. 12 is a diagram showing an example in which identification information of a new X-ray detector is delivered to a workstation paired with an X-ray detector, according to an example embodiment.

FIG. 12 is a diagram showing an example in which identification information of a new X-ray detector is delivered to a workstation paired with an X-ray detector, according to an example embodiment.

Referring to FIG. 12, while the workstation 300 is paired with a first X-ray detector 200-1 (①), the mobile device 100 may deliver new identification information to the workstation 300 (②). Here, the new identification information is identification information of an X-ray detector other than the first X-ray detector 200-1. In this example, the identification information refers to identification information of a second X-ray detector 200-2.

Also, when the second X-ray detector 200-2 is tagged with the mobile device 100, the mobile device 100 may acquire the identification information of the second X-ray detector 200-2.

Each of the first X-ray detector 200-1 and the second X-ray detector 200-2 corresponds to the X-ray detector 200 according to the above-described example embodiment, and the terms "first" and "second" only refer to an order in which the detectors are paired with the workstation 300.

The first X-ray detector 200-1 and the second X-ray detector 200-2 have the above-described configuration and only perform the above-described operation, and the first X-ray detector 200-1 and the second X-ray detector 200-2 may have different types of detector information or different models.

When the new identification information is delivered, the workstation 300 releases the previous pairing (③). That is, the workstation 300 releases the pairing with the first X-ray detector 200-1.

When the workstation 300 sends a pairing request to the second X-ray detector 200-2 (④) and the second X-ray detector 200-2 responds to the request, the workstation 300 and the second X-ray detector 200-2 are paired (⑤).

In summary, whenever the workstation 300 receives new identification information from the mobile device 100, the workstation 300 releases the previous pairing and attempts a new pairing. When new identification information is again received from the mobile device 100 after the workstation 300 is paired with the second X-ray detector 200-2, the workstation 300 may release the pairing with the second X-ray detector 200-2 and retry a new pairing.

Figure 13:
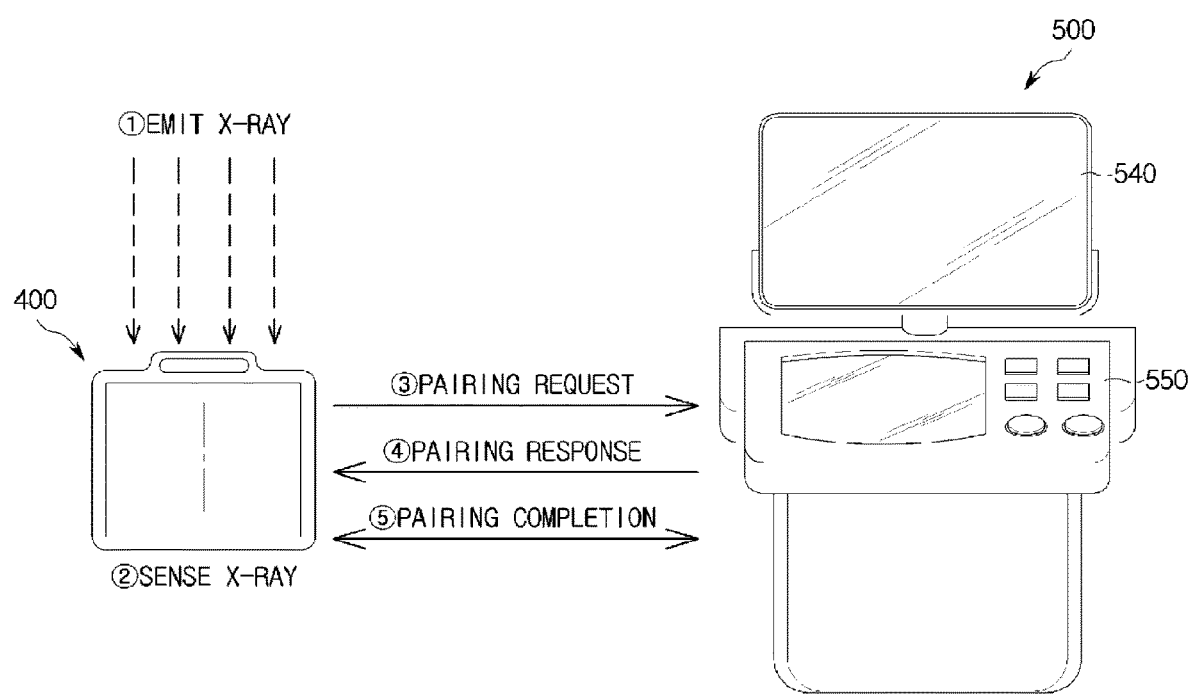
FIG. 13 is a diagram showing a process in which an X-ray detector and a workstation are paired, according to another example embodiment.
Figure 14:
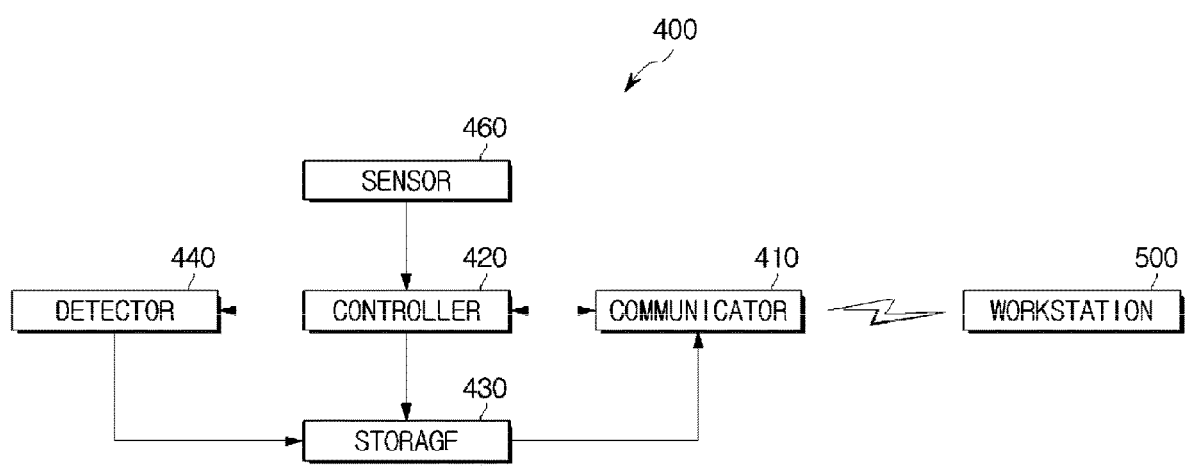
FIGS. 14 and 15 are control block diagrams of an X-ray detector and a workstation, according to another example embodiment.
Figure 15:
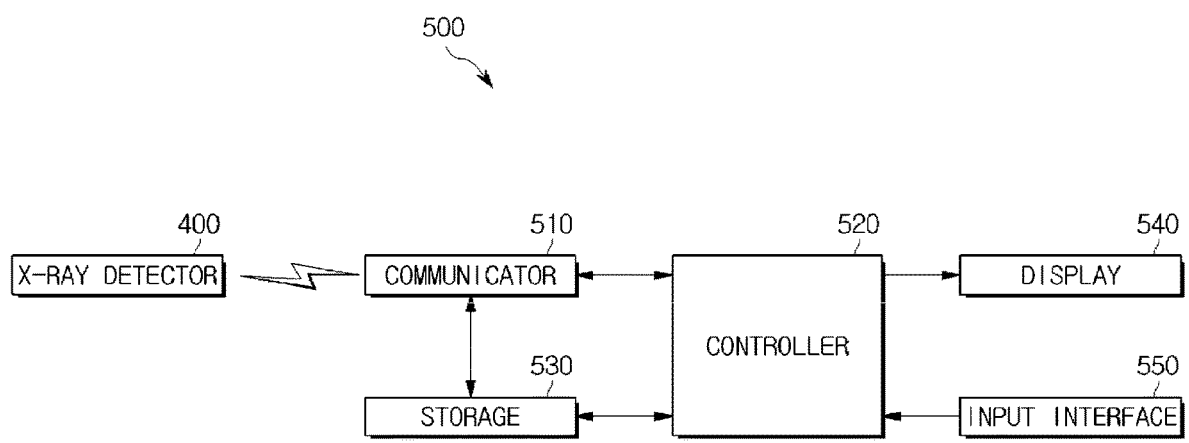

FIG. 13 is a diagram showing a process in which an X-ray detector and a workstation are paired, according to another example embodiment, and FIGS. 14 and 15 are control block diagrams of an X-ray detector and a workstation, according to another example embodiment. Even in this example embodiment, default elements, such as a THU, an imaging stand, an imaging table, and a mounting unit, of the X-ray imaging apparatus may be the same as those in the above example embodiment.

According to another example embodiment, an X-ray emitted from the THU 10 may activate an X-ray detector or a pairing operation of the X-ray detector.

Referring to FIG. 13, when an X-ray from the THU 10 is incident on an X-ray detector 400 (①), the X-ray detector 400 senses the X-ray (②) and sends a pairing request to a workstation 500. When the workstation 500 responds to the pairing request (④), the X-ray detector 400 and the workstation 500 are paired and may send and receive signals to and from each other.

That is, in this example embodiment, an X-ray incident on the X-ray detector 400 may act as a trigger signal that activates the X-ray detector 400. Here, activation of the X-ray detector 400 means that the X-ray detector 400 may send a pairing request to the workstation 500. That is, the activation may refer to activation of a communicator 410.

Alternatively, the activation of the X-ray detector 400 may include turning the X-ray detector 400 on. In this case, when a sensor 460 that is always turned on senses incidence of an X-ray, a detector 440 may be activated and generate X-ray data, and the communicator 410 may be activated and send a pairing request to the workstation 500.

The X-ray data generated by the detector 440 may be stored in a storage 430. When the X-ray detector 400 and the workstation 500 are paired, the communicator 410 may send the X-ray data stored in the storage 430 to the workstation 500. Accordingly, even when X-ray imaging is started before the X-ray detector 400 and the workstation 500 are paired, X-ray data may be sent to the workstation 500 without loss.

Alternatively, an X-ray emission for activating the communicator 410 may precede an X-ray emission for actual X-ray imaging. The X-ray emission may be performed with low dose. After the communicator 410 of the X-ray detector 400 is activated and the pairing between the X-ray detector 400 and the workstation 500 is achieved, the actual X-ray imaging may be performed. Here, the preceding X-ray emission may be a pre-shot that is provided to control X-ray exposure parameters according to characteristics of an object.

Referring to FIG. 14, the X-ray detector 400 according to another example embodiment includes the communicator 410 that communicates with the workstation 500 to send and receive signals, a controller 420 that controls an operation of the X-ray detector 400, the storage 430 that stores identification information and X-ray data of the workstation 500, the detector 440 that detects an X-ray and converts the detected X-ray into X-ray data, and the sensor 460 that senses incidence of an X-ray.

The communicator 410 may include a communication module that performs short-range wireless communication. For example, the communicator 410 may employ WFD to communicate with the workstation 500. However, the communication method employed by the communicator 410 is not limited to WFD. The communicator 410 may employ another short-range communication method such as Wireless LAN, Wi-Fi, Bluetooth, ZigBee, UWB, IrDA, BLE, and NFC, and may include a communication module corresponding to the employed communication method.

A description of the detector 440 is the same as that of the detector 240 shown in FIG. 4 and thus will be omitted herein.

The sensor 460 may include a sensor capable of sensing an X-ray. As an example, the sensor 460 may include an ionization chamber used as an automatic exposure control (AEC) sensor.

The ionization chamber is filled with gas that interacts with an X-ray and generates photoelectrons, Auger electrons, or fluorescence photons. Helium, Nitrogen, Neon, Argon, Krypton, Xenon, or the like may be employed as the gas filling the ionization chamber.

When an X-ray interacts with the gas filling the ionization chamber and an electric current is generated, the controller 420 may determine that the X-ray is incident and may control the communicator 410 to send a pairing request to the workstation 500.

To this end, identification information, such as an IP address or MAC address, of the workstation 500 may be prestored in the storage 430. When an X-ray is incident on the X-ray detector 200, the communicator 410 may send a pairing request to the workstation 500 having the identification information stored in the storage 430.

Alternatively, the communicator 410 may include a BLE module or beacon and transmit a signal including the identification information of the X-ray detector 400 within a range instead of specifying a target that will receive the signal. The workstation 500 located in the range may acquire the identification information of the X-ray. The workstation 500 that has acquired the identification information of the X-ray detector 400 may send a pairing request to the X-ray detector 400.

In this case, a communication module for sending the identification information of the X-ray detector 400 to the workstation 500 may be different from or the same as a communication module for sending and receiving signals between the X-ray detector 400 and the workstation 500 that are paired.

For example, when the communication modules are different, a beacon or BLE module may be used as the communication module for sending the identification information of the X-ray detector 400 to the workstation 500, and a WFD module may be used as the communication module for sending and receiving signals between the X-ray detector 400 and the workstation 500.

Referring to FIG. 15, the workstation 500 according to an example embodiment includes a communicator 510 that communicates with the X-ray detector 400 to send and receive signals, a controller 520 that controls an operation of the workstation 500, a storage 530 that stores identification information and X-ray image signals of the workstation 500, a display 540, and an input interface 550.

The communicator 510 may include a communication module that performs short-range wireless communication. For example, the communicator 510 may employ WFD to communicate with the X-ray detector 400. However, the communication method employed by the communicator 510 is not limited thereto. The communicator 510 may employ another short-range communication method such as Wireless LAN, Wi-Fi, Bluetooth, ZigBee, UWB, IrDA, BLE, and NFC, and may include a communication module corresponding to the employed communication method.

However, the communicator 510 has a communication module corresponding to the communication module included in the communicator 410 of the X-ray detector 400. For example, when the communicator 410 of the X-ray detector 400 includes a beacon or BLE module and a WFD module, the communicator 510 of the workstation 500 may include a BLE module and a WFD module.

Also, the communicator 510 may further include a wireless communication module for sending and receiving signals to and from any one or any combination of a base station of a mobile communication network, an external device, and a server such as a PACS.

When a pairing request is received from the X-ray detector 400, the communicator 510 finishes a pairing process in response to the request. When the pairing is completed, the workstation 500 and the X-ray detector may send and receive signals to and from each other.

Also, when the identification information of the X-ray detector 400 is received from the X-ray detector 400, the workstation 500 may send a pairing request to the X-ray detector 400 corresponding to the identification information.

When X-ray imaging is started, the communicator 410 of the X-ray detector 400 sends X-ray data acquired from a detected X-ray to the workstation 500. The communicator 510 of the workstation 500 may receive the X-ray data. The controller 520 may generate an X-ray image from which a lesion can be identified by processing the received X-ray data using detector information. The display 540 may display the generated X-ray image, and the input interface 550 receives a control command associated with X-ray imaging and X-ray image generation from a user as an input.

The storage 530 may temporarily or non-temporarily store identification information, detector information, X-ray data, and an X-ray image of the X-ray detector 200.

Also, the communicator 510 may send the generated X-ray image to a PACS or other terminals.

Figure 16A:
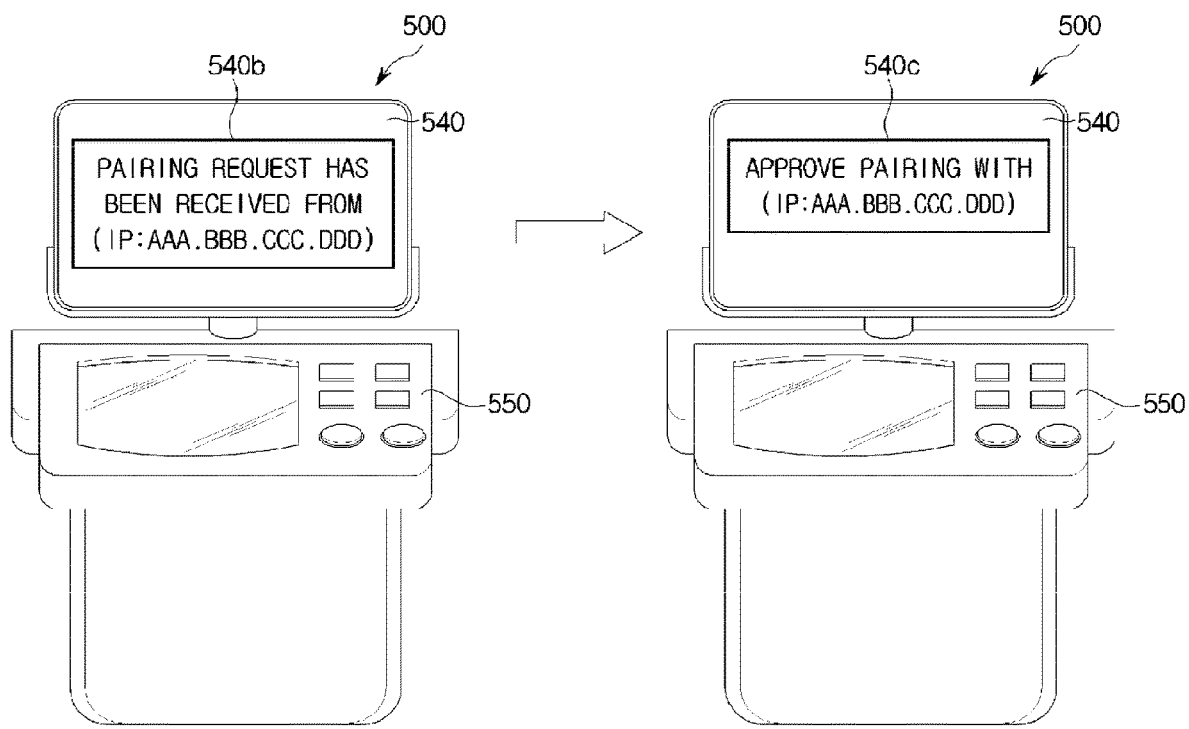
FIGS. 16A and 16B are diagrams showing examples of a screen that may be displayed on a display of a workstation when the workstation receives a pairing request from an X-ray detector, according to an example embodiment.
Figure 16B:
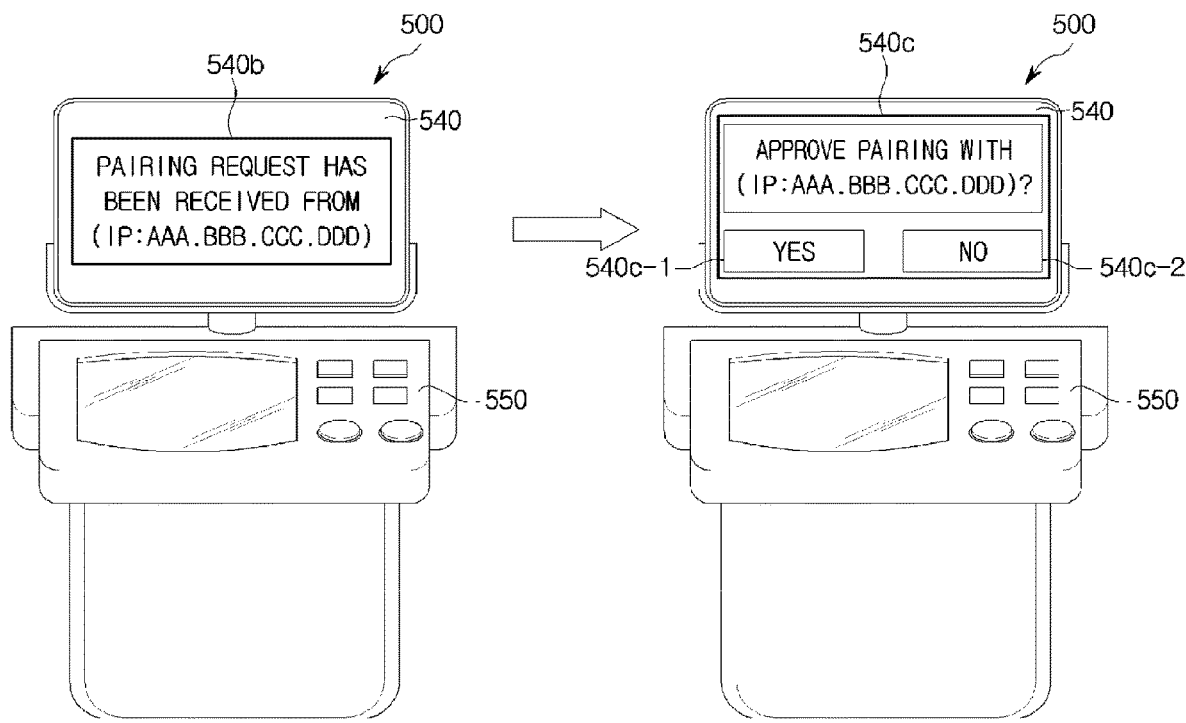

FIGS. 16A and 16B are diagrams showing examples of a screen that may be displayed on a display of a workstation when the workstation receives a pairing request from an X-ray detector, according to an example embodiment.

When the X-ray detector 400 sends a pairing request to the workstation 500, a reception screen 540a that informs a user that the pairing request has been received from the X-ray detector 400 may be displayed on the display 540 of the workstation 300 as shown on the left side of FIG. 16A.

Even when the user does not perform a separate operation, the workstation 500 may automatically send a pairing response to approve the pairing. In this case, an approval screen 540b that informs the user that the pairing has been approved may be displayed on the display 540. The user may recognize a current status by viewing the screens 540a and 540b displayed on the display 540.

Alternatively, as shown in FIG. 16B, an approval request screen 540c may be displayed on the display 540 before the pairing is approved, thus allowing the user to select whether to approve the pairing. When the user selects a "yes" button 540*c*-1, the workstation 500 may send a pairing response to the X-ray detector 400, and thus the pairing may be completed. When the user selects a "no" button 540*c*-2, the workstation 500 does not send a pairing response to the X-ray detector 400.

FIGS. 16A and 16B show examples in which IP addresses, each of which is identification information for pairing, are displayed on the screens 540*b* and 540*c*. However, recognition identification information may also be displayed. For example, when an X-ray detector that is not suitable for X-ray imaging intended to be performed is mounted, a user may confirm that the unsuitable X-ray detector has been mounted by viewing recognition identification information displayed on the screens 540*b* and 540*c* and selecting the "no" button 540*c*-2.

Also, when the X-ray detector 400 sends its own identification information, a screen that asks the user whether to send a pairing request to the X-ray detector 400 may be displayed on the display 540 of the workstation 500 to receive the user's selection or a screen that informs the user that pairing is being requested may be displayed on the display 540 while sending a pairing request without the user's selection.

Figure 17A:
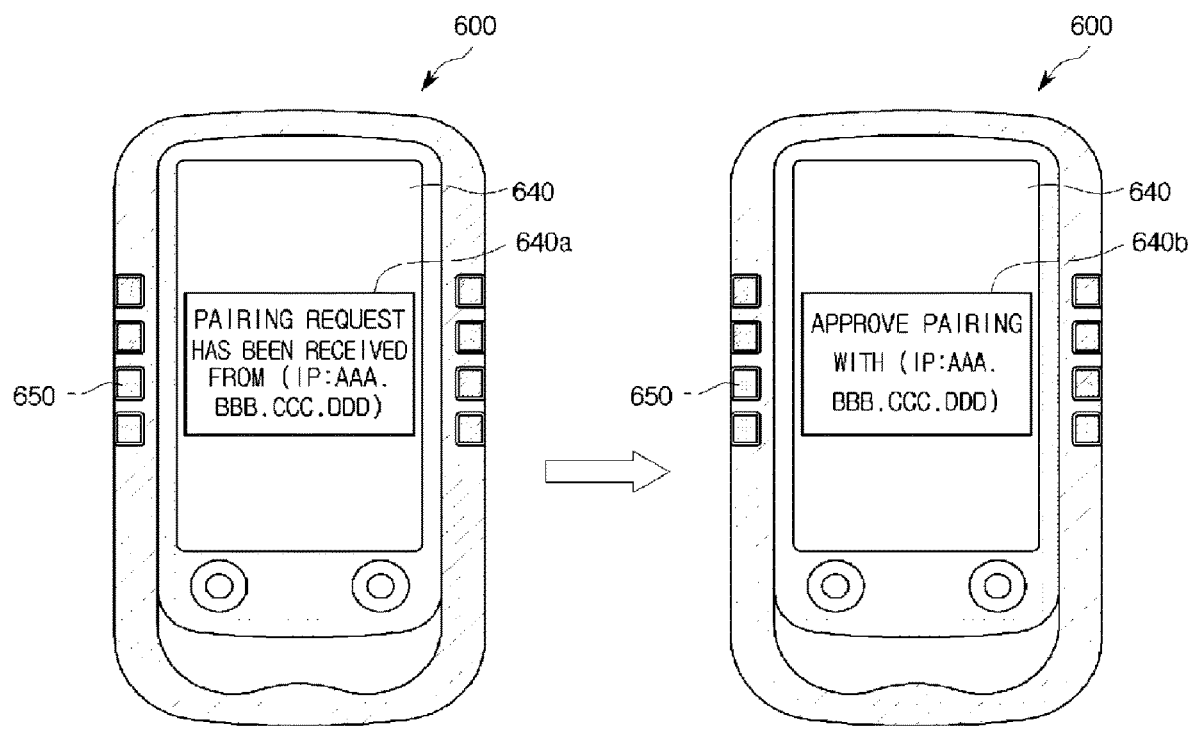
FIGS. 17A and 17B are diagrams showing examples of a screen that may be displayed when a tube head unit receives a pairing request from an X-ray detector, according to an example embodiment.
Figure 17B:
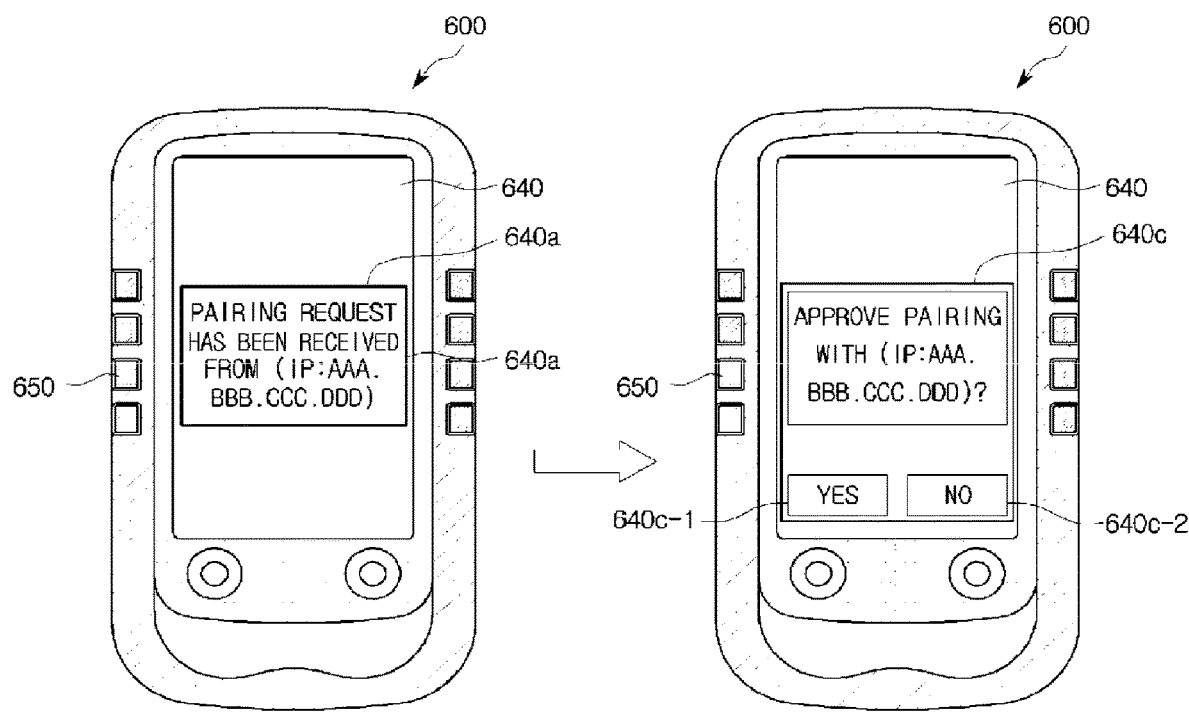
Figure 18:
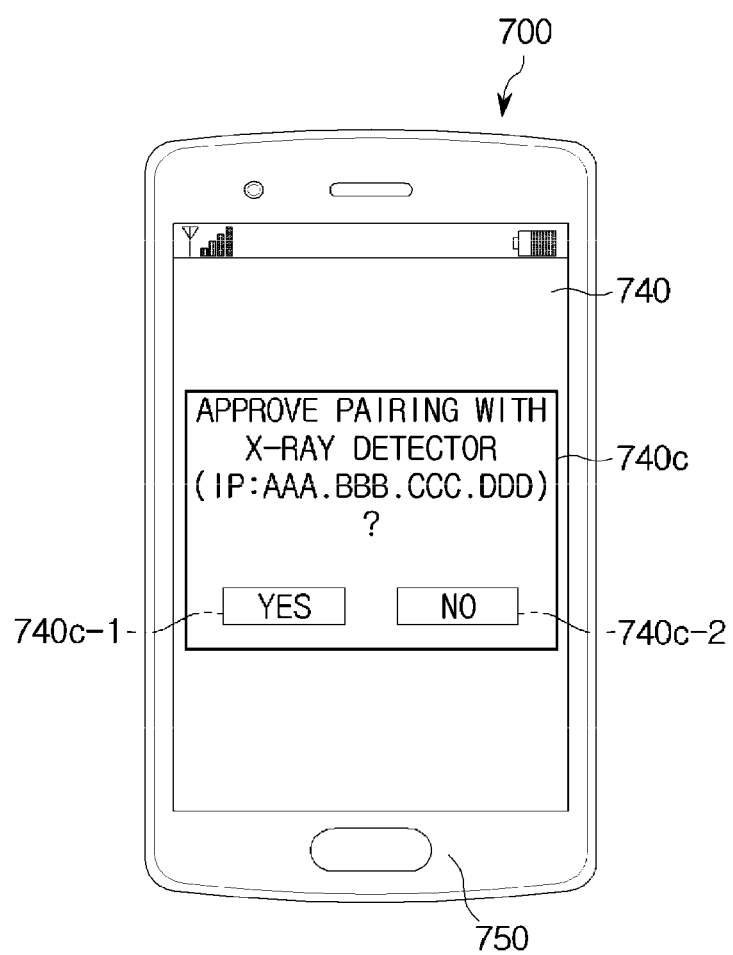
FIG. 18 is a diagram showing an example of a pairing approval screen displayed on a mobile device, according to an example embodiment.

FIGS. 17A and 17B are diagrams showing examples of a screen that may be displayed when a THU receives a pairing request from an X-ray detector, according to an example embodiment, and FIG. 18 is a diagram showing an example of a pairing approval request screen displayed on a mobile device, according to an example embodiment.

Like the aforementioned example embodiment, when a control panel 600 of the THU 10 is included in a host device to perform some or all functions of the workstation 500, the X-ray detector 400 may send a pairing request to the control panel 600. When the control panel 600 that has received the pairing request responds to the pairing, the pairing between the X-ray detector 400 and the control panel 600 may be immediately approved and completed.

Alternatively, as shown in FIG. 17A, a reception screen 640*a* that informs a user that a pairing request has been received from the X-ray detector 400 may be displayed on the display 640 of the control panel 600. In this case, the control panel 600 may also approve the pairing without the user's manipulation. At this point, an approval screen 640*b* that informs the user that the pairing has been approved may be displayed on the display 640 of the control panel 600.

Alternatively, as shown in FIG. 17B, a pairing approval request screen 640*c* may be displayed on the display 640 before the pairing is approved, thus allowing the user to approve the pairing. When the user manipulates the input interface 650 to select a "yes" button 640*c*-1, the pairing is approved, and the control panel 600 sends a response to the X-ray detector 400. When the user selects a "no" button 640*c*-2, the control panel 600 does not send a response.

Alternatively, when a pairing request is received from the X-ray detector 400, the workstation 500 or the control panel 600 may send a pairing approval request to a mobile device 700. In this case, as shown in FIG. 18, a pairing approval request screen 740*c* may be displayed on a display 740 of the mobile device 700.

Information regarding the mobile device 700 may be prestored in the workstation 500. That is, the workstation 500 may send a pairing approval request to the mobile device 700 having the information prestored in the workstation 500.

When a user manipulates an input interface 750 to select a "yes" button 740*c*-1, the mobile device 700 may send a pairing approval signal to the workstation 500 or the control panel 600.

When the workstation 500 or the control panel 600 receives the pairing approval signal, the pairing between the X-ray detector 400 and the workstation 500 or the control panel 600 is completed. When the workstation 500 or the control panel 600 has not sent a pairing response to the X-ray detector 400 upon reception of the pairing approval signal, the workstation 500 or the control panel 600 may send the pairing response after receiving the pairing approval signal. When the pairing response has already been sent, the pairing is completed and signals may be sent or received.

When the user selects a "no" button 740*c*-2, a pairing refusal signal may be sent to the workstation 500 or the control panel 600. In this case, although the workstation 500 or the control panel 600 has sent the pairing response to the X-ray detector 400, the pairing is not completed.

In the aforementioned example embodiment, the X-ray detector 400 may not include the sensor 460. In this case, when the detector 440 detects an X-ray and generates X-ray data, the controller 420 activates the communicator 410 to send a pairing request or identification information to the workstation 500.

Regardless of whether the sensor 460 is included, incidence of an X-ray acts as a trigger signal or an activation signal. However, incidence of an X-ray is sensed by the sensor 460 when the sensor 460 is included, and the incidence of the X-ray is sensed by the detector 440 when the sensor 460 is not included. An example in which an X-ray detector does not include the sensor will be described below.

Figure 19:
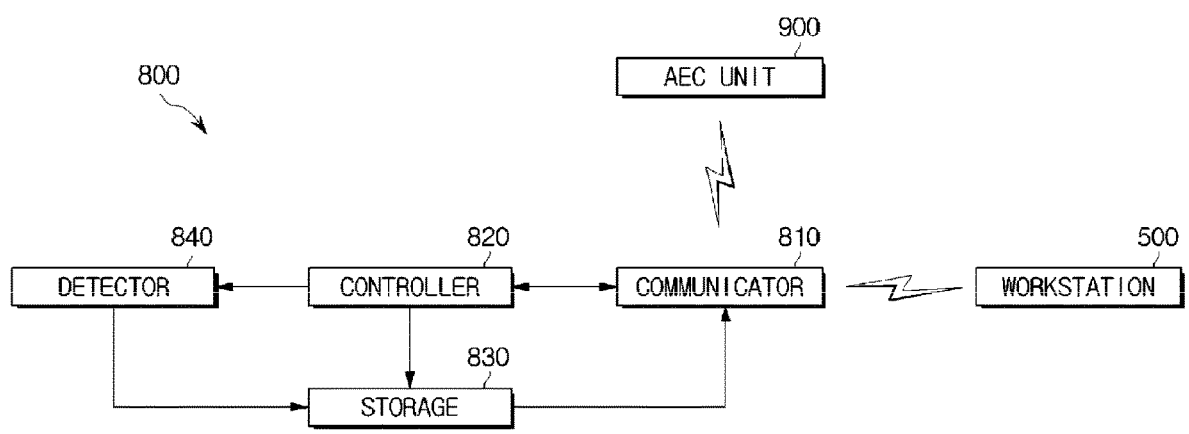
FIG. 19 is a control block diagram of an X-ray detector according to still another example embodiment.
Figure 20:
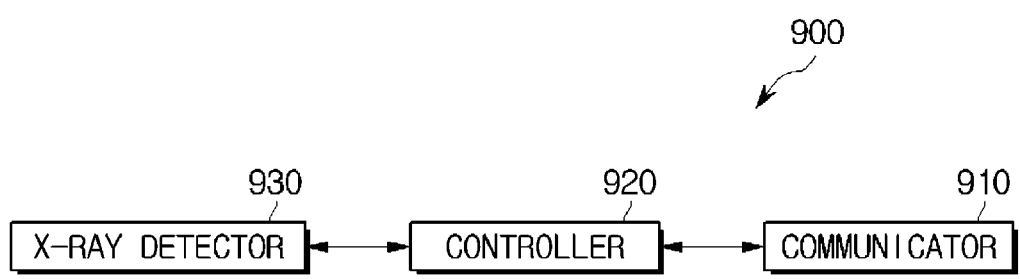
FIG. 20 is a control block diagram of an automatic exposure control (AEC) unit according to an example embodiment.
Figure 21:
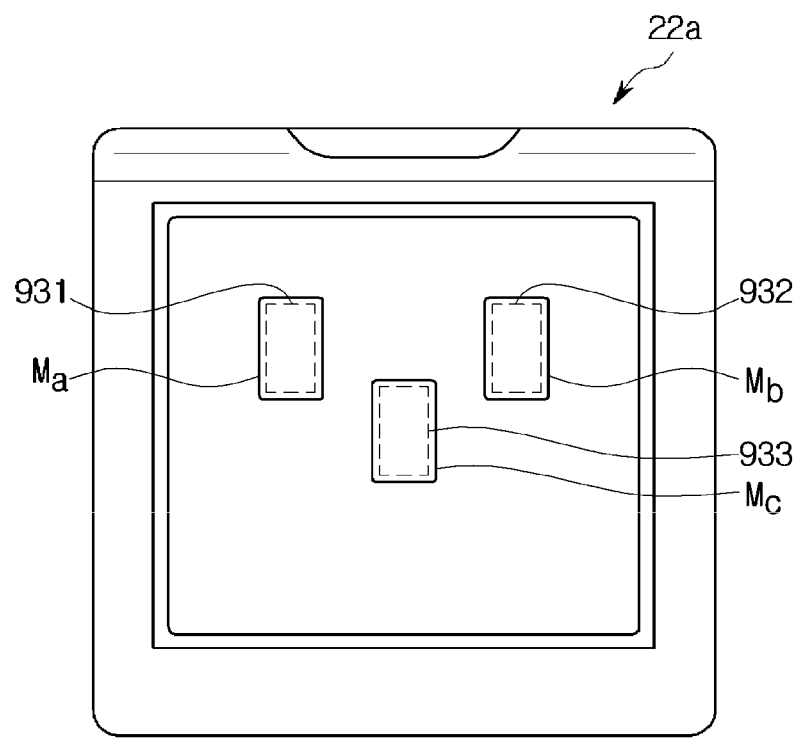
FIG. 21 is a diagram showing a configuration of an AEC unit according to an example embodiment.

FIG. 19 is a control block diagram of an X-ray detector according to still another example embodiment, FIG. 20 is a control block diagram of an AEC unit according to an example embodiment, and FIG. 21 is a diagram showing a configuration of an AEC unit according to an example embodiment.

Referring to FIG. 19, an X-ray detector 800 according to still another example embodiment includes a communicator 810 that communicates with the workstation 500 and an AEC unit 900, a controller 820 that controls an operation of the X-ray detector 800, a storage 830 that stores identification information and X-ray data of the workstation 500, and a detector 840 that detects an X-ray and converts the detected X-ray into X-ray data.

In the aforementioned example embodiment, the X-ray detector 800 includes the sensor 460 that senses an X-ray. However, in this example embodiment, the X-ray detector 800 does not include a separate sensor and receives an activation signal from the AEC unit 900 provided in a mounting unit.

First, a configuration and an operation of the AEC unit 900 will be described with reference to FIGS. 20 and 21.

An X-ray imaging apparatus may perform AEC to prevent an object from being excessively exposed to radiation. To this end, an X-ray imaging apparatus 1 may include the AEC unit 900 that senses an X-ray dose.

As shown in FIG. 20, the AEC unit 900 includes an X-ray detector 930 that senses incidence of an X-ray, a communicator 910 that sends a signal to the X-ray detector 800 and the workstation 500 when the X-ray is incident, and a controller 920 that controls the AEC unit 900.

The AEC unit 900 may be provided inside the detector mounting unit 22*a*. This example will be described using the detector mounting unit 22*a* of the imaging table 22. However, the AEC unit 900 may be provided in the detector mounting unit 21a of the imaging stand 21.

FIG. 21 is a front view of the detector mounting unit 22a, according to an example embodiment. The X-ray detector 930 of the AEC unit 900 may include a plurality of AEC sensors 931, 932, and 933 that independently sense an X-ray dose. As an example, each of the AEC sensors may be implemented as an ionization chamber. A description of the ionization chamber is the same as described in the aforementioned example embodiment.

The most accurate automatic exposure control is possible when an AEC sensor is located at the center of an X-ray imaging portion. To place the center of the X-ray imaging portion at a position corresponding to the AEC sensor or select an AEC sensor placed at the center of the X-ray imaging portion, markers Ma, Mb, and Mc indicating positions of the plurality of AEC sensors 931, 932, and 933 may be displayed on a surface of the detector mounting unit 22a.

FIG. 21 shows that a total of three AEC sensors are provided, that is, two AEC sensors are provided at an upper portion and one AEC sensor is provided at a lower portion, but this is an example. A larger or smaller number of AEC sensors may be provided.

When an X-ray is incident on an AEC sensor, an electric current is generated. When the electric current is generated by the AEC sensor, the controller 920 may send an activation signal to the X-ray detector 800 through the communicator 910. The activation signal may be a trigger signal for starting a pairing operation of the X-ray detector 800.

Also, the communicator 910 may deliver a signal corresponding to the electric current generated by the AEC sensor to the workstation 500.

The controller 520 of the workstation 500 determines whether an X-ray dose that is currently incident exceeds a critical dose on the basis of the delivered signal. When the X-ray dose exceeds the critical dose, the controller 520 may send a cutoff signal to a high-voltage generator that supplies high voltage to the THU 10 to stop generating the X-ray.

The communicator 910 may send signals to each of the X-ray detector 800 and the workstation 500 using the same communication method or different communication methods. For the latter, the communicator 910 may include different communication modules.

For example, the communicator 910 may send signals to the X-ray detector 800 using NFC and send signals to the workstation 500 using Wi-Fi or WFD.

There is no limitation on a method in which the communicator 910 sends signals to the X-ray detector 800 and the workstation 500.

Referring to FIG. 19 again, the communicator 810 sends a pairing request to the workstation 500 when an activation signal is received from the AEC unit 900. When the workstation 500 responds to the request and pairing is achieved, the X-ray detector 800 may send detector information such as calibration information, remaining battery capacity, size, resolution, pixel size, and read-out rate to the workstation 500.

Also, X-ray data generated by the detector 840 may be sent to the workstation 500. Depending on a start point of X-ray imaging, the X-ray data may be sent after being stored in the storage 830 or in real time.

Also, the communicator 810 may send signals to each of the AEC unit 900 and the workstation 500 using the same communication method or different communication methods. For the latter, the communicator 810 may include different communication modules. In each case, the communication module included in the communicator 810 corresponds to the communicator 910 of the AEC unit 900 and the communicator 510 of the workstation 500.

An example of a pairing method between an X-ray detector and a workstation according to an aspect will be described below. In the pairing method between an X-ray detector and a workstation, the X-ray detectors 200, 400, and 800, the workstations 300 and 500, the control panels 80 and 600, the mobile devices 100 and 700, and the AEC unit 900 that have been described above may be used. Accordingly, the descriptions with reference to FIGS. 1 to 19 may be applied to the pairing method to be described below.

Figure 22:
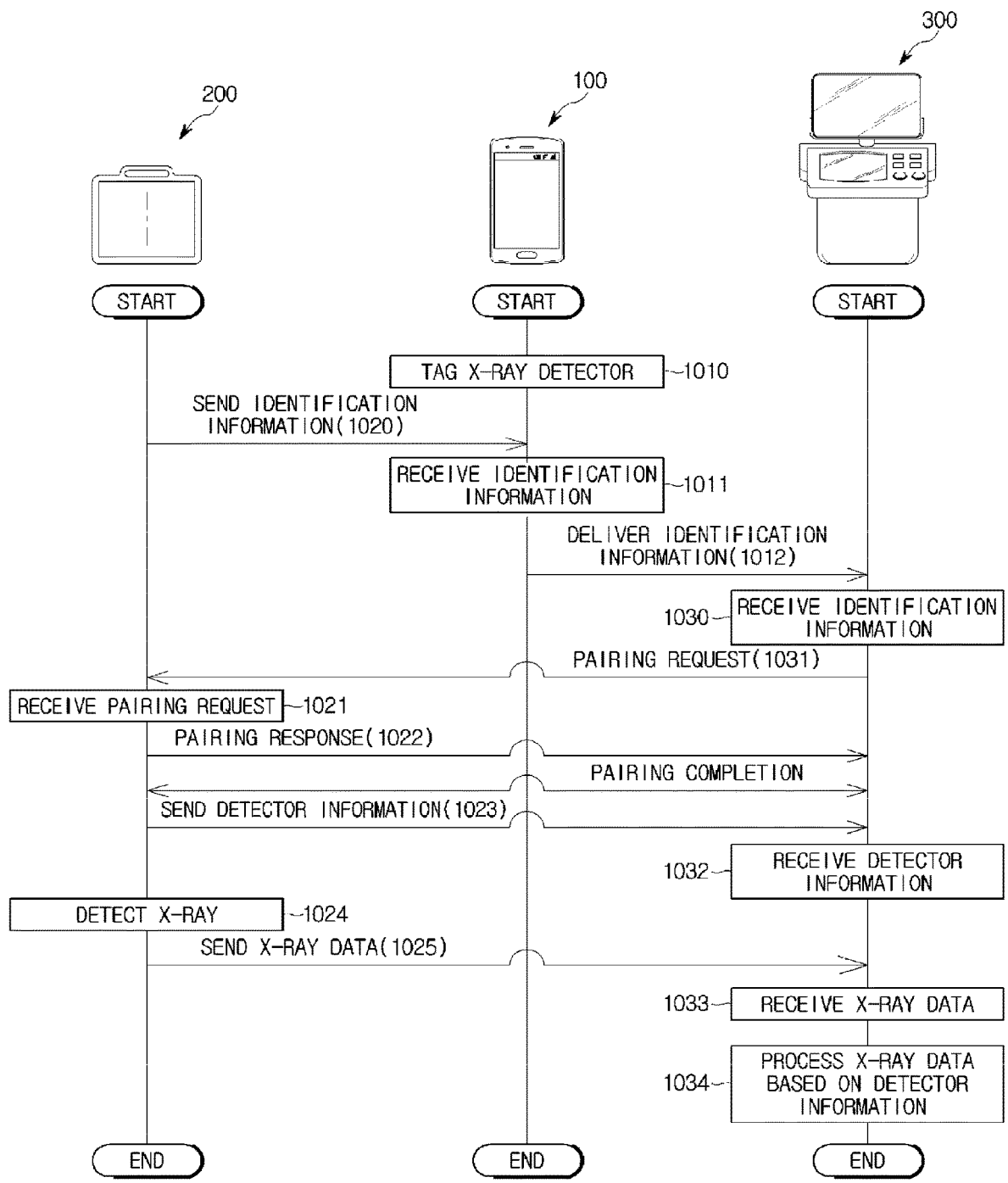
FIG. 22 is a flowchart of a pairing method of an X-ray detector, according to an example embodiment.

FIG. 22 is a flowchart of a pairing method of an X-ray detector, according to an example embodiment.

Referring to FIG. 22, the X-ray detector 200 is tagged with the mobile device 100 (1010). In this case, the communicator 110 of the mobile device 100 may include a communication module configured to read information through a tagging operation, such as an NFC module or an RFID reader. The tagging operation may include authentication by a user tagging the X-ray detector 200 to be used for X-ray imaging.

The X-ray detector 200 that is tagged with the mobile device 100 sends its own identification information to the mobile device 100 (1020). The identification information may include information for communication, such as an IP address or a MAC address. Also, in addition to the identification information, the X-ray detector 200 may further send detector information such as size, resolution, pixel size, read-out rate, and calibration information.

When the detector information is sent, the display 140 of the mobile device 100 may display the sent detector information, thus allowing the user to select whether to perform pairing. The user may confirm the detector information displayed on the display 140, determine whether the X-ray detector 200 is suitable for X-ray imaging to be performed, and select whether to approve the pairing.

When the mobile device 100 receives the identification information from the X-ray detector 200 (1011), the mobile device 100 delivers the received identification information to the workstation 300 (1012). Also, when the detector information is also received from the X-ray detector 200, the mobile device 100 may deliver the detector information in addition to the identification information.

A communication method used when the identification information is received from the X-ray detector 200 and a communication method used when the identification information is delivered to the workstation 300 may be different or the same. As an example of the former, the identification information may be delivered to the workstation 300 through BLE. To this end, the communicator 110 of the mobile device 100 may include a beacon or BLE module.

The workstation 300 receives the identification information of the X-ray detector 200 from the mobile device 100 (1030) and sends a pairing request to the X-ray detector 200 having the received identification information (1031). Before the pairing request is sent, the user may select whether to perform the pairing. That is, the X-ray detector 200 may select whether to send the pairing request. In this case, a screen that checks whether to perform pairing with the X-ray detector may be displayed by displaying recognition identification information used by the user to easily recognize the X-ray detector on the display 340.

The X-ray detector 200 receives the pairing request (1021) and sends a pairing response (1022) to finish pairing with the workstation 300. That is, communication is established between the X-ray detector 200 and the workstation 300, and the X-ray detector 200 and the workstation 300 may send and receive signals.

The pairing between the X-ray detector 200 and the workstation 300 may not be completed immediately, but may be completed after the pairing is finally approved. For example, when approval of the pairing is not received from the user before the mobile device 100 delivers the identification information of the X-ray detector 200 to the workstation 300 or before the workstation 300 sends the pairing request to the X-ray detector 200, the workstation 300 that has received the pairing response from the X-ray detector may send a pairing approval request to the mobile device 100. The mobile device 100 may display a screen for receiving approval of the pairing from the user. When the user inputs a pairing approval command, the mobile device 100 may send a pairing approval signal to the workstation 300. When the workstation 300 receives the pairing approval signal, the pairing between the X-ray detector 200 and the workstation 300 may be completed.

When the mobile device 100 does not deliver the detector information to the workstation 300, the X-ray detector 200 paired with the workstation 300 may send the detector information (1023), and the workstation 300 may receive the detection information (1032).

When X-ray imaging is performed and an X-ray is emitted from the THU 10, the X-ray detector 200 detects the X-ray (1024) and generates X-ray data, and sends the generated X-ray data to the workstation 300 paired with the X-ray detector 200 (1025).

The workstation 300 receives the X-ray data (1033) and processes the received X-ray data on the basis of the detector information of the X-ray detector 200 to generate an effective X-ray image (1034).

In the aforementioned example, the pairing between the X-ray detector 200 and the workstation 300 has been described. However, the X-ray detector 200 may be paired with the control panel 80 of the THU 10. In this case, the pairing method between the X-ray detector 200 and the workstation 300 may also be applied to the X-ray detector 200 and the control panel 80.

The pairing method of an X-ray detector according to an example embodiment may include some or all of the steps that have been described with reference to FIG. 19. For example, the pairing method may include steps 1010, 1011, and 1012 that are performed using the mobile device 100, steps 1020, 1021, 1022, 1023, and 1024 that are performed using the X-ray detector 200, or steps 1030, 1031, 1032, and 1033 that are performed using the workstation 300.

Figure 23:
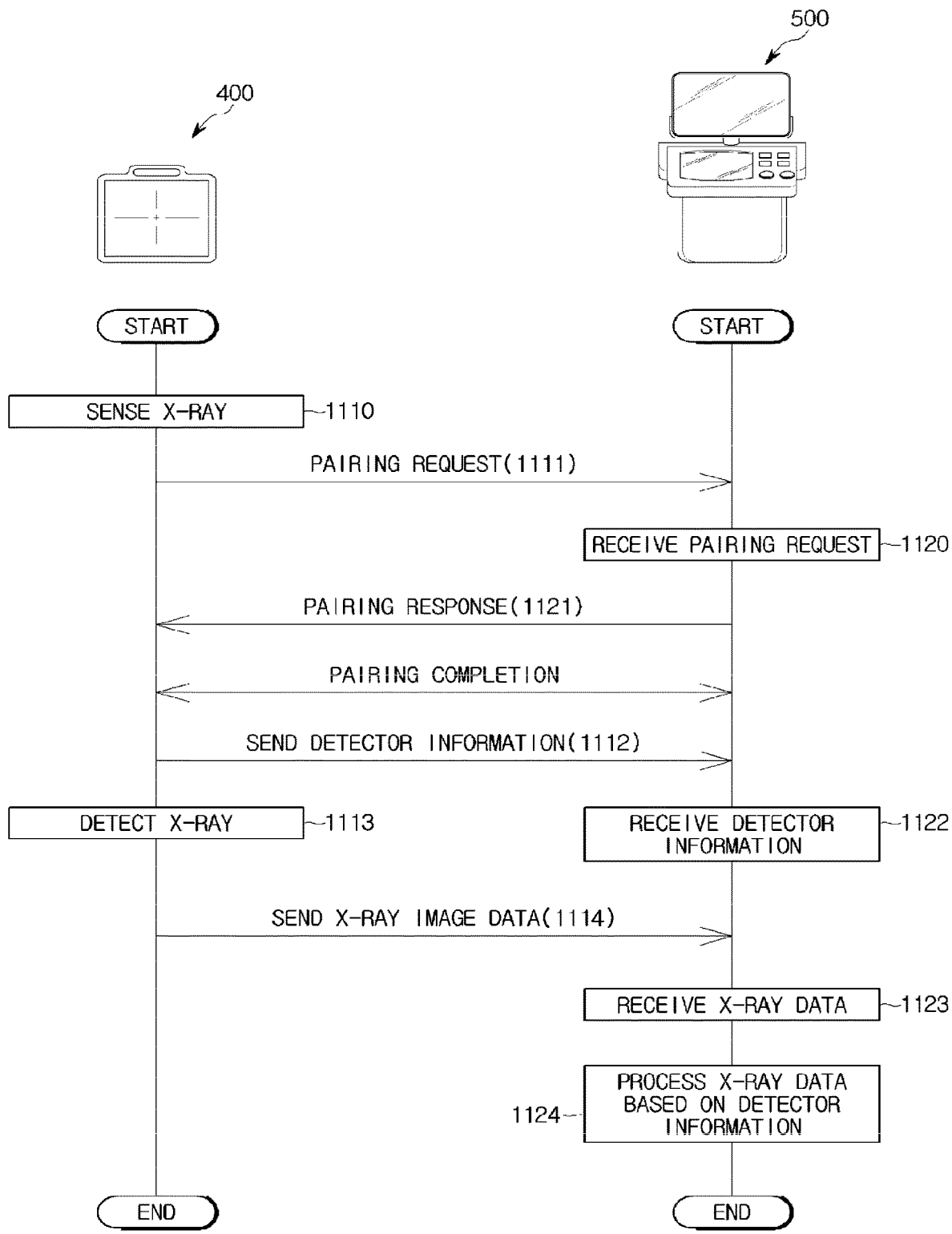
FIG. 23 is a flowchart of a pairing method of an X-ray detector, according to another example embodiment.

FIG. 23 is a flowchart of a pairing method of an X-ray detector, according to another example embodiment.

Referring to FIG. 23, when the X-ray detector 400 senses an X-ray (1110), a communication module for communicating with the workstation 500 is activated to send a pairing request to the workstation 500 (1111). In this case, the sensor 460 provided in the X-ray detector 400 may sense incidence of the X-ray.

The workstation 500 receives the pairing request (1120) and sends a pairing response to the X-ray detector 400.

Likewise, pairing between the X-ray detector 400 and the workstation 500 may not be completed immediately, but may be completed after the pairing is finally approved. For example, before or after the workstation 500 sends the pairing response (1121) to the X-ray detector 400, the workstation 500 that has received the pairing request from the X-ray detector may send a pairing approval request to the mobile device 700. The mobile device 700 may display a screen for receiving approval of the pairing from the user. When the user inputs a pairing approval command, the mobile device 100 may send a pairing approval signal to the workstation 500. When the workstation 500 receives the pairing approval signal, the pairing between the X-ray detector 400 and the workstation 500 may be completed. When the workstation 500 has not sent the pairing response to the X-ray detector 400 upon reception of the pairing approval signal, the workstation 500 may send the pairing response to the X-ray detector 400 and finish the pairing.

When the pairing between the X-ray detector 400 and the workstation 500 is completed, the X-ray detector 400 may send detector information to the workstation 500 (1112), and the workstation 500 may receive the detector information (1122).

The X-ray sensed in step 1110 may be emitted as a pre-shot for pairing activation or by a main shot for X-ray imaging. For the former, the main shot is made after the pairing is completed, and the X-ray detector 400 may detect the X-ray (1113) and generate X-ray data, and transmit the generated X-ray data to the workstation 500 (1114). For the latter, the sensing of the X-ray and the detection of the X-ray (1113) may be simultaneously achieved, and the generated X-ray data may be stored in the storage 430 and then sent to the workstation 500 when the X-ray detector 400 and the workstation 500 are paired.

The workstation 500 receives the X-ray data (1123) and processes the received X-ray data on the basis of the detector information to generate an effective X-ray image (1124).

According to still another example embodiment, the X-ray detector 800 may receive an activation signal from the AEC unit 900 provided for controlling an X-ray dose to send a pairing request to the workstation 500 instead of including a separate sensor. Subsequent operations are the same as those in the aforementioned example embodiment.

Some of the operations of the mobile devices 100 and 700, the operations of the workstations 300 and 500, the operations of the control panels 80 and 600, and the pairing method of an X-ray detector that have been described may be stored as a program in a computer-readable recording medium. That is, the computer-readable recording medium may store a program including an instruction for executing some of the aforementioned operations.

The recording medium may be a magnetic recording medium such as a floppy disk and a hard disk or an optical recording medium such as a CD-ROM and a DVD. However, the type of the recording medium is not limited to the above-described example.

The recording medium may be included in a server that provides an application or program. The mobile devices 100 and 700, the control panels 80 and 600, or the workstations 300 or 500 may access the server through a communication protocol such as the Internet and download the program.

According to the aforementioned example embodiments, it is possible to facilitate pairing of the X-ray detector and the workstation without a process in which a user directly inputs information on the X-ray detector.

It is also possible to enable more accurate pairing of an X-ray detector and a workstation by preventing an error that may occur while a user inputs information on the X-ray detector.

It is also possible to reduce a work load of a user by using a light weight mobile device or emitting only an X-ray to automatically perform pairing without needing to directly move an X-ray detector to pair the X-ray detector with a workstation.

According to the X-ray detector, the mobile device, the host device, the X-ray imaging apparatus, and the method of pairing an X-ray detector with a host device according to an aspect, it is possible to simply and accurately pair an X-ray detector with a host device without a task of a user directly entering information regarding the X-ray detector into a host device or the like.

In addition, the example embodiments may also be implemented through computer-readable code and/or instructions on a medium, e.g., a computer-readable medium, to control at least one processing element to implement any above-described embodiments. The medium may correspond to any medium or media that may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more example embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The above-described subject matter of the example embodiments is to be considered illustrative and not restrictive, and numerous other modifications and example embodiments can be devised by those skilled in the art that will fall within the spirit and scope of the principles of the example embodiments. Accordingly, the example embodiments and drawings of the example embodiments are to be considered descriptive and not restrictive of the example embodiments, and do not limit the scope of the example embodiments. The scope of the example embodiments may be determined by the following claims and their appropriate legal equivalents.

What is claimed is:

1. An X-ray detector comprising:
    a memory storing identification information indicating an Internet Protocol (IP) address or a Media Access Control (MAC) address of the X-ray detector;
    a communicator including a near field communication (NFC) module; and
    a controller configured to control the communicator to:
        send the identification information indicating the IP address or the MAC address of the X-ray detector through near field communication via the NFC module when the X-ray detector is tagged,
        receive, through a communication protocol other than near field communication, a pairing request from a workstation that received the sent identification information indicating the IP address or the MAC address of the X-ray detector, and
        send, through the communication protocol other than near field communication, a response to the received pairing request to the workstation, to pair the X-ray detector and the workstation together.

2. The X-ray detector according to claim 1, wherein
the X-ray detector comprises a battery to provide power to the X-ray detector,
the memory stores detector information indicating battery capacity of the battery, and
the controller is configured to control the communicator to send the detector information indicating the battery capacity of the battery, in addition to the identification information indicating the IP address or the MAC address of the X-ray detector, through near field communication via the NFC module when the X-ray detector is tagged.

3. The X-ray detector according to claim 1, wherein
the memory stores detector information indicating a size of the X-ray detector, and
the controller is configured to control the communicator to send the detector information indicating the size of the X-ray detector, in addition to the identification information indicating the IP address or the MAC address of the X-ray detector, through near field communication via the NFC module when the X-ray detector is tagged.

4. The X-ray detector according to claim 1, wherein
the memory stores detector information indicating a resolution of the X-ray detector, and
the controller is configured to control the communicator to send the detector information indicating the resolution of the X-ray detector, in addition to the identification information indicating the IP address or the MAC address of the X-ray detector, through near field communication via the NFC module when the X-ray detector is tagged.

5. The X-ray detector according to claim 1, wherein the X-ray detector is taggable by the workstation so that the controller is configured to control the communicator to send the identification information indicating the IP address or the MAC address of the X-ray detector through near field communication via the NFC module to the workstation when the X-ray detector is tagged by the workstation.

6. The X-ray detector according to claim 1, wherein the X-ray detector is taggable by the a mobile device that communicates with the workstation so that the controller is configured to control the communicator to send the identification information indicating the IP address or the MAC address of the X-ray detector through near field communication via the NFC module to the mobile device when the X-ray detector is tagged by the mobile device.

* * * * *

UNITED STATES PATENT AND TRADEMARK OFFICE
CERTIFICATE OF CORRECTION

PATENT NO. : 11,134,906 B2  
APPLICATION NO. : 16/838524  
DATED : October 5, 2021  
INVENTOR(S) : Park et al.

It is certified that error appears in the above-identified patent and that said Letters Patent is hereby corrected as shown below:

In the Claims

Column 28, Line 48:
Claim 6, before "mobile" change "the a" to "a"

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*